United States Patent
Nabatame et al.

(10) Patent No.: US 8,086,010 B2
(45) Date of Patent: Dec. 27, 2011

(54) MEDICAL IMAGE DIAGNOSIS APPARATUS AND THE CONTROL METHOD THEREOF

(75) Inventors: Takeo Nabatame, Otawara (JP); Tomiya Sasaki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1185 days.

(21) Appl. No.: 11/771,422

(22) Filed: Jun. 29, 2007

(65) Prior Publication Data

US 2008/0123924 A1    May 29, 2008

(30) Foreign Application Priority Data

Jun. 30, 2006    (JP) .................................. 2006-181217

(51) Int. Cl.
G06K 9/00    (2006.01)

(52) U.S. Cl. ................ 382/131; 382/128; 378/4; 378/21

(58) Field of Classification Search .................. 382/128, 382/131, 173; 378/4, 16, 21; 250/455; 128/922
See application file for complete search history.

(56) References Cited

U.S. PATENT DOCUMENTS

| | | | | |
|---|---|---|---|---|
| 4,117,337 A | * | 9/1978 | Staats | 378/17 |
| 4,158,776 A | * | 6/1979 | Barrett | 378/20 |
| 5,081,656 A | * | 1/1992 | Baker et al. | 378/21 |
| 5,197,474 A | * | 3/1993 | Englund et al. | 600/415 |
| 5,482,042 A | * | 1/1996 | Fujita | 600/428 |
| 5,594,772 A | * | 1/1997 | Toki et al. | 378/114 |
| 5,612,985 A | * | 3/1997 | Toki et al. | 378/4 |
| 5,651,043 A | * | 7/1997 | Tsuyuki et al. | 378/65 |
| 5,740,225 A | * | 4/1998 | Nabatame | 378/65 |
| 6,014,419 A | * | 1/2000 | Hu | 378/4 |
| 6,022,143 A | * | 2/2000 | Helmreich | 378/181 |
| 6,023,799 A | * | 2/2000 | Wirth et al. | 5/601 |
| 6,289,073 B1 | * | 9/2001 | Sasaki et al. | 378/4 |

(Continued)

FOREIGN PATENT DOCUMENTS

JP    2004-180846    7/2004

(Continued)

OTHER PUBLICATIONS

Sonke et al. "Variability of Four Dimensional Computed Tomography Patient Models" Int. J Radiation Oncology Biol. Phys. vol. 70 No. 2 pp. 590-598 (2008).*

(Continued)

*Primary Examiner* — Jason M Repko
*Assistant Examiner* — Mia M Thomas
(74) *Attorney, Agent, or Firm* — Oblon, Spivak, McClelland, Maier & Neustadt, L.L.P.

(57) ABSTRACT

Obtain a tomographic image of a patient table in advance in a state in which the object is not placed on the patient table. Obtain a tomographic image of the patient table with the object placed on the patient table. This tomographic image consists of an image of a patient table. The displacement calculation part determines the vertical displacement of images of the patient table in a non-loaded state and the tomographic image of the patient table in a loaded state. Meanwhile, markers are placed on the side of the patient table to indicate the displacement detecting position (reference position). The corrected image-forming part corrects the vertical positions of image data of the tomographic image in the loaded state based on the calculated displacement.

7 Claims, 8 Drawing Sheets

U.S. PATENT DOCUMENTS

| | | | | |
|---|---|---|---|---|
| 6,298,111 | B1* | 10/2001 | Ozaki | 378/8 |
| 6,334,708 | B1* | 1/2002 | Kosugi | 378/197 |
| 6,363,136 | B1* | 3/2002 | Flisikowski et al. | 378/154 |
| 6,381,297 | B1* | 4/2002 | Hsieh | 378/15 |
| 6,405,072 | B1* | 6/2002 | Cosman | 600/426 |
| 6,424,854 | B2* | 7/2002 | Hayashi et al. | 600/415 |
| 6,473,634 | B1* | 10/2002 | Barni | 600/425 |
| 6,490,477 | B1* | 12/2002 | Zylka et al. | 600/429 |
| 6,631,284 | B2* | 10/2003 | Nutt et al. | 600/427 |
| 6,775,352 | B2* | 8/2004 | Toth et al. | 378/108 |
| 6,850,588 | B2* | 2/2005 | Arenson et al. | 378/16 |
| 6,865,250 | B2* | 3/2005 | Londt et al. | 378/8 |
| 6,873,676 | B2* | 3/2005 | Hsieh | 378/4 |
| 6,894,281 | B2* | 5/2005 | Such et al. | 250/367 |
| 6,895,105 | B2* | 5/2005 | Wollenweber | 382/131 |
| 6,969,194 | B1* | 11/2005 | Nafstadius | 378/197 |
| 6,987,828 | B2* | 1/2006 | Horiuchi | 378/16 |
| 7,113,569 | B2* | 9/2006 | Okumura et al. | 378/150 |
| 7,167,739 | B2* | 1/2007 | Van De Rijdt et al. | 600/415 |
| 7,194,122 | B2* | 3/2007 | Faber et al. | 382/131 |
| 7,283,606 | B2* | 10/2007 | Kalender et al. | 378/8 |
| 7,292,673 | B2* | 11/2007 | Kroner et al. | 378/20 |
| 7,332,722 | B1* | 2/2008 | Tran et al. | 250/363.09 |
| 7,359,477 | B2* | 4/2008 | Lauritsch et al. | 378/4 |
| 7,394,927 | B2* | 7/2008 | Proksa et al. | 382/154 |
| 7,421,058 | B2* | 9/2008 | Popescu et al. | 378/20 |
| 7,532,704 | B2* | 5/2009 | Hempel | 378/19 |
| 7,634,827 | B2* | 12/2009 | Gagneur et al. | 5/601 |
| 7,641,660 | B2* | 1/2010 | Lakin et al. | 606/87 |
| 7,689,022 | B2* | 3/2010 | Weiner et al. | 382/133 |
| 7,792,231 | B2* | 9/2010 | Popescu | 375/354 |
| 7,810,187 | B2* | 10/2010 | Van Es et al. | 5/601 |
| 7,870,624 | B1* | 1/2011 | Winston | 5/611 |
| 2001/0048732 | A1* | 12/2001 | Wilson et al. | 378/21 |
| 2002/0131544 | A1* | 9/2002 | Aradate et al. | 378/4 |
| 2003/0016781 | A1* | 1/2003 | Huang | 378/41 |
| 2003/0068075 | A1* | 4/2003 | Faber et al. | 382/131 |
| 2003/0073893 | A1* | 4/2003 | Hsieh | 600/407 |
| 2004/0068167 | A1* | 4/2004 | Hsieh et al. | 600/407 |
| 2004/0086084 | A1* | 5/2004 | Murray et al. | 378/196 |
| 2004/0101179 | A1* | 5/2004 | Suryanarayanan et al. | 382/128 |
| 2004/0247070 | A1* | 12/2004 | Ali et al. | 378/4 |
| 2005/0100126 | A1* | 5/2005 | Mistretta et al. | 378/15 |
| 2005/0111762 | A1* | 5/2005 | Mathew et al. | 382/309 |
| 2005/0253584 | A1* | 11/2005 | Campagna | 324/318 |
| 2005/0254621 | A1* | 11/2005 | Kalender et al. | 378/46 |
| 2006/0036160 | A1* | 2/2006 | Altman et al. | 600/415 |
| 2006/0043293 | A1* | 3/2006 | Doi et al. | 250/310 |
| 2006/0083345 | A1* | 4/2006 | Hsieh et al. | 378/17 |
| 2006/0173257 | A1* | 8/2006 | Nagai et al. | 600/323 |
| 2007/0019781 | A1* | 1/2007 | Haras | 378/4 |
| 2007/0053478 | A1* | 3/2007 | Tsuyuki et al. | 378/4 |
| 2007/0081624 | A1* | 4/2007 | Nabatame | 378/19 |
| 2007/0104310 | A1* | 5/2007 | Nottling et al. | 378/4 |
| 2007/0110290 | A1* | 5/2007 | Chang et al. | 382/128 |
| 2007/0253528 | A1* | 11/2007 | Ning et al. | 378/15 |
| 2008/0095301 | A1* | 4/2008 | Kohler et al. | 378/4 |
| 2008/0317204 | A1* | 12/2008 | Sumanaweera et al. | 378/65 |
| 2008/0319317 | A1* | 12/2008 | Kamiyama et al. | 600/443 |
| 2009/0003515 | A1* | 1/2009 | Naidu et al. | 378/14 |
| 2009/0257557 | A1* | 10/2009 | Sumanaweera et al. | 378/65 |
| 2009/0310845 | A1* | 12/2009 | Ogawa et al. | 382/132 |
| 2010/0034342 | A1* | 2/2010 | Forthmann et al. | 378/15 |
| 2010/0045088 | A1* | 2/2010 | Kunou | 297/354.1 |
| 2010/0074404 | A1* | 3/2010 | Ito | 378/42 |
| 2010/0183215 | A1* | 7/2010 | Sakai et al. | 382/132 |
| 2010/0195884 | A1* | 8/2010 | Werthner | 382/131 |
| 2010/0228769 | A1* | 9/2010 | Dorn et al. | 707/769 |

FOREIGN PATENT DOCUMENTS

| | | |
|---|---|---|
| JP | 2005-291814 | 10/2005 |
| WO | WO 2004/081864 A2 * | 9/2004 |
| WO | WO 2007046036 * | 4/2007 |
| WO | WO 2008042564 * | 4/2008 |
| WO | WO 2008047308 * | 4/2008 |

OTHER PUBLICATIONS

Geckle et al. "Correction for Patient and Organ Movement in SPECT: Application to Exercise Thallium-201 Cardiac Imaging" vol. 29, No. 4 Apr. 1988 pp. 1-10.*

* cited by examiner

MEDICAL IMAGE DIAGNOSIS APPARATUS AND THE CONTROL METHOD THEREOF

BACKGROUND OF THE INVENTION

1. Field of the Invention

The present invention relates to a medical image diagnosis apparatus and the control method thereof that forms a medical image of an object. In particular, it relates to techniques that correct displacement of an image caused by bending of the patient table (patient table deflection) on which an object is placed.

2. Description of the Related Art

Conventionally, medical image diagnosis apparatuses such as the X-ray CT apparatus and nuclear medical diagnosis apparatus (PET, SPECT, etc.) have been widely used (refer to Japanese Unexamined Patent Application Publication No. 2004-180846 as an example). In recent years, diagnostic systems that combine an X-ray CT apparatus with a nuclear medical diagnosis apparatus, such as a PET-CT, are also in practical use (refer to Japanese Unexamined Patent Application Publication No. 2005-291814 as an example).

An example of construction of a general medical image diagnosis apparatus (X-ray CT apparatus) is shown in FIG. 1 and FIG. 2. This X-ray CT apparatus 1000 comprises a gantry 2, examination table 3, computer 4, monitor 5, and input device 6.

The monitor 5 and input device 6 are used as a console 7 for the X-ray CT apparatus 1000 (refer to FIG. 2). The monitor 5 comprises any display device such as an LCD (Liquid Crystal Display) or CRT display (Cathode Ray Tube display). The input device 6 comprises any input device, including a keyboard, mouse, trackball, control panel, touch panel, etc.

The gantry 2 houses a turnable support 21 as shown in FIG. 2. The X-ray tube 22 and X-ray detector 23 are supported by the support 21. The X-ray tube 22 generates X-rays based on a specified tube voltage and the tube current applied by a high-voltage transformer assembly 24 and delivers an X-ray fan-beam and cone-beam to an object P located inside the opening 2A of the gantry 2. The X-ray detector 23 is supported at a location opposite the X-ray tube 22 over the opening 2A. The X-ray detector 23 comprises arrayed multiple X-ray detection elements that detect dosage of the X-ray beam transmitted at the object P.

The support 21 is rotated along the circumference of the opening 2A by a support drive section 25. The X-ray tube 22 and X-ray detector 23 rotate along with the support 21 as it rotates in a unified manner to scan the object P with X-ray beam. This allows the X-ray dosage of the X-ray beam transmitted at the object P to be detected from various directions. The data (detection signal) of the transmitted X-ray dosage detected by the X-ray detector 23 is sent to data acquisition part 26.

The data acquisition part 26 is a so-called DAS (Data Acquisition System) that comprises arrayed data acquisition elements, similar to each X-ray detection element of the X-ray detector 23, which collect data (detection signal) of the transmitted X-ray dosage detected by the X-ray detector 23. The data acquisition part 26 performs amplification and A/D conversion processing of the collected data and transmits the data to the computer 4.

The support drive section 25 not only rotates the support 21 as described above but also operates to tilt the support 21 toward the object P.

The examination table 3, as shown in FIG. 1, comprises a patient table 31 on which an object P is placed and an examination table base 32 that supports the patient table 31. The examination table base 32 houses a patient table drive 33 (refer to FIG. 2) that moves the patient table 31 variously in an anteroposterior direction (in the direction of the arrow in FIG. 1, horizontal direction; z-direction), up and down direction (vertical direction; y-direction), longitudinal direction (horizontal direction perpendicular to the anteroposterior direction; x-direction). The abovementioned anteroposterior direction (z-direction) is the direction of the body axis of the object P on the patient table 31.

The computer 4 comprises, for example, a general-purpose computer. The computer 4 houses a microprocessor such as a CPU, memory such as RAM or ROM, a high-capacity storage unit such as a hard disk drive, and an interface that sends and receives data to and from other devices. The other devices may be a gantry 2, examination table 3, console 7, and another computer on a network not shown here, etc.

The computer 4 comprises a device control part 41 and image processing part 42. The device control part 41 controls the operation of each part of the X-ray CT apparatus 1. For example, the device control part 41 executes control of rotation and tilting of the support 21 by the support drive section 25, operational control of the X-ray tube 22 by a high-voltage transformer assembly 24, operational control of the X-ray detector 23, operational control of the data acquisition part 26, moving operational control of the patient table 31 by the patient table drive 33, etc.

The image processing part 42 applies preprocessing to the transmitted X-ray dosage data collected by the gantry 2 to generate projection data. Furthermore, the image processing part 42 reconstructs the image data of the tomographic image of the object P based on the projection data.

For such medical image diagnosis apparatus, the problem of deflection off the patient table 31 caused by the weight of the object P has been indicated as described in Japanese Unexamined Patent Application Publication No. 2004-180846 and Japanese Unexamined Patent Application Publication No. 2005-291814, etc. More specifically, when the object P is not placed on the patient table 31, the patient table 31 does not bend (significantly) when moving the patient table 31 in the z-direction (refer to FIG. 3A). However, when the object P is placed thereon, the end side of the patient table 31 (the side near the opening of the gantry 2) is bent downward (y-direction) because of the weight of the object P (refer to FIG. 3B). The quantity of deflection (downward displacement, etc.) of the patient table 31 varies, depending on the body weight, etc., of the object P and the position where the object P is placed on the patient table 31. The quantity of deflection also varies, depending on the position of the patient table 31 (distance of the patient table 31).

When X-ray beam scanning is performed with the patient table 31 bent in this manner, the body axis of the object P, which should be horizontal, is placed tilted at the opening 2A. Then, as shown in FIG. 4, displacement Δy in the y-direction occurs at the slice location A, and the displacement Δy will be reflected in the reconstruction image (where Δy=y−y0:y0=y-coordinate value of the patient table 31 when the object P is not placed thereon; y=y-coordinate value of the patient table 31 when the object P is placed thereon).

Moreover, the cross-section at the slice location A, which is preset in the planning stage of scanning, will be tilted as shown in FIG. 3B, because the body axis of the object P tilts along with the obliquity of the patient table 31. With imaging in such a tilted position, the tomographic image of the cross-section at the slice location α, shown in FIG. 3B, will be reconstructed.

As described above, making an image diagnosis using a less-accurate reconstructing image different from the cross-section at the planning stage of the scan may lead to inaccuracy in diagnosis. For example, there is concern about deterioration of treatment planning for radiotherapy whereby radiation is delivered to an affected area such as a tumor.

Particularly, in recent years, a small lesion can be detected with the improvement of the image resolution of the medical image diagnosis apparatus. In order to deliver radiation to this tiny target accurately, the location of the target should be precisely pinpointed from an image, and then the actual target location in the object P corresponding to the pinpointed location needs to be specified.

When using an image containing a displacement caused by patient table deflection, it is relatively easy to pinpoint the location of a lesion in the image, but it is difficult to specify the location in the object P with a high degree of accuracy in relation to the location pinpointed from the image, because a state in which the object is placed on the patient table of the object P is different from a state in which the object is placed on the patient table of the object P during the treatment planning stage (in general, the object P is placed with his/her body axis being horizontal).

A wide variety of efforts have been taken to deal with such patient table deflection, for example, placing a member (a patient table support member such as a shore) that supports the patient table 31, or that the treatment planner properly adjusts the X-ray irradiated site by considering the effect of the patient table deflection.

Meanwhile, radiation therapy called IMRT (Intensity Modulated Radiation Therapy) has been performed in recent years. IMRT combines multiple beams to allow radiation to adjust its level, so tumor tissue is exposed to radiation intensively whereas the adjacent normal tissue receives lower irradiance level. This allows stronger radiation to be delivered to the tumor without increasing side effects.

In IMRT, an image is taken with a medical image diagnosis apparatus first to specify the location and shape of the tumor, and the irradiated area and intensity will be determined accordingly. Next, mark the body surface of the object and take a medical image to confirm the irradiated area. The irradiated area and intensity will be adjusted if needed (it is called positioning). Then, the object is placed on a special treatment device to perform radiation therapy.

Marking is done by a seal applied to the body surface or drawing a mark with a pen. There are visible markings that appear in a medical image as well as invisible markings that do not. For the former, for example, a seal made of a material with X-ray absorption that is different from that of human body and patient table.

When using an X-ray CT apparatus, for example, mark three points on the body surface to specify a location to be matched with the scanning center (the rotation center of the X-ray tube and X-ray detector) and capture an image, figure out the location and shape of the tumor, and confirm the irradiated area, etc. The location of the tumor and the irradiated area will be learned as a specified location by the marking, that is, the displacement from the scanning center. Marking may be applied to indicate the irradiation center (isocenter).

A construction is disclosed to Japanese Unexamined Patent Application Publication No. 2004-180846 that detects the displacement of the patient table and corrects the relative position of the patient table and the slice direction based on the detected result. The displacement of the patient table here is detected by using sensors installed in a longitudinal direction at specified distances on the patient table and a CCD camera that captures the condition of the displacement of the patient table. In addition, the relative position is corrected by lifting and lowering the examination table (patient table) and changing the height and tilt angle of the gantry.

A construction is also disclosed in Japanese Unexamined Patent Application Publication No. 2004-180846 that detects the displacement of the patient table by using similar sensors, and based on the detected result, extracts an image data of which the relative position of the patient table and the scan location is corrected from the multiple image data collected at multiple locations.

An invention described in Japanese Unexamined Patent Application Publication No. 2005-291814 is related to aligning image data collected from each medical image diagnosis apparatus for complex diagnosis system such as PET-CT.

Specifically, first, the location information of the projection data for X-ray CT and the location information of absorption compensation data are extracted, and the projection data for nuclear medicine having functional data will be corrected based on this absorption compensation data. Next, based on the displacement of the extracted projection data for X-ray CT and absorption compensation data, both or one of the projection data for X-ray CT and corrected projection data for nuclear medicine (alternatively, move both or one of the tomographic image for X-ray CT and corrected tomographic image for nuclear medicine) are moved. Then, projection data and absorption compensation data are determined by X-ray CT apparatus and nuclear medical diagnosis apparatus respectively with reference to an object having no change in location over time, and projection data and absorption compensation data for nuclear medicine are determined with each radiation that transmitted the same location of the object so that the heightwise displacement between a tomographic image for X-ray CT and a tomographic image for PET caused by the deflection from the patient table is corrected.

A construction is disclosed in Japanese Unexamined Patent Application Publication No. 2005-291814 that installs the same radiation source on a nuclear medical diagnosis apparatus as the radioactive agent that is administered to an object when imaging for nuclear medicine to be irradiated to the object to determine absorption compensation data based on the transmitted radiation delivered to an object.

When dealing with the above mentioned problem of the displacement of the patient table with the conventional medical image diagnosis apparatus described above, the following inconvenience will occur.

First of all, when applying the above mentioned patient table supporting member or the construction with the sensors installed on the patient table (Japanese Unexamined Patent Application Publication No. 2004-180846), a major alteration will be needed for the general hardware configuration of the medical image diagnosis apparatus (e.g., the patient table supporting member and the sensors need to be added.). On the other hand, considering the price of the apparatus, etc., it would be a heavy burden for the user to purchase a new apparatus with such construction preapplied.

A construction is disclosed in Japanese Unexamined Patent Application Publication No. 2004-180846, that deals with the displacement of the patient table by tilting the tablet top and the gantry. When performing a helical scan by an X-ray CT apparatus, for example, as the tilt caused by the displacement of the patient table varies from the location to location of the patient table, the angle of tilting the patient table and gantry should be controlled to change sequentially along with the tilt of the patient table changes. However, it is not easy to control such movements accurately. In addition, when applying the construction of changing the angle of tilting the patient table, the patient as the object may feel uncomfortable as the tilt angle of the object is also changed accordingly.

Japanese Unexamined Patent Application Publication No. 2004-180846 assumes that when calculating the quantity of deflection between the reference positions (according to the document, the positions where the sensors are placed) placed on the patient table, the direction of the displacement of all of each point is parallel.

However, in order to calculate the quantity of deflection accurately based on this assumption, further assumptions are needed including that the quantity of deflection of the each point is negligibly small and the distance between the reference positions is short enough.

When applying the former assumption, the patient table must be strengthened, but if the strength of the patient table is enhanced, other problems may arise, including reduction of sensitivity to gamma ray detection due to the increased absorption of gamma rays by the patient table as described in Japanese Unexamined Patent Application Publication No. 2005-291814.

On the other hand, when applying the latter assumption, multiple sensors should be installed on the patient table which also causes other problems such as increase in cost, complex control and more maintenance.

Furthermore, assuming that the direction of the displacement of all of the each point is parallel, a problem occurs in that the tilt condition of the patient table cannot be accurately detected. Particularly, if the distance between the sensors is large or the object is heavy, the angle of tilting the patient table between the sensors is expected to change. However, the change in the angle of tilting the patient table between the sensors cannot be detected, because only the tilt angle of the line connecting the sensors can be calculated according to the computation method of the document.

In addition, when a treatment planner is dealing with the deflection of the patient table by displacing the x-ray irradiation site by considering the effect of the patient table deflection, the treatment planner has to change the X-ray irradiated site based on his/her own experience, etc., not on objective data of the quantity of deflection. Therefore, it is difficult to ensure the accuracy of the irradiated site.

Moreover, because the construction described in Japanese Unexamined Patent Application Publication No. 2005-291814 is for matching an image for nuclear medicine with an image of an X-ray CT, it cannot be applied to cases in which a standalone X-ray CT apparatus is used.

In addition, when performing IMRT, the irradiated area must be determined precisely and the radiation must be delivered to the tumor accurately. For this purpose, the location in an image must be corresponded to the actual location in the object with a high degree of accuracy. For example, when X-ray CT apparatus is used, the correspondence is ensured by deeming the location specified by marking to be the scanning center.

In IMRT, however, because images are taken with a medical image diagnosis apparatus and radiation irradiation is performed with a special treatment device, a state in which the object is placed on the patient table when radiation is delivered to the object may be different from the condition when the image is taken and the irradiated area specified by the image may not match the actual irradiated area because of the effect by the patient table deflection. Such misalignment not only prevents intensive radiation delivery to the tumor but also exposes normal tissue to radiation. In particular, it is difficult to detect misalignment of the irradiated area when the marking is invisible.

SUMMARY OF THE INVENTION

This invention is intended to provide a medical image diagnosis apparatus and its control method that can correct the displacement of the patient table without implementing a major alteration to the hardware configuration of the apparatus.

In a first aspect of the invention, a medical image diagnosis apparatus comprising: a patient table; a data acquisition part configured to scan the patient table in a non-loaded state in which an object is not placed on the patient table to acquire first scan data and to scan the patient table and an object in a loaded state in which the object is placed on the patient table to acquire second scan data; an image data-forming part configured to form a first image based on the first scan data and a second image based on the second scan data; a displacement calculation part configured to calculate displacement of the patient table in the non-loaded state and in loaded state based on the first image and the second image; and a correction part configured to correct the position of the second image based on the displacement.

According to the first aspect, the scanning takes place for both the state in which the object is not placed on the patient table and the state in which the object is placed on the patient table. In a state in which the object is not placed on the patient table, the patient table is scanned to acquire the first scan data, and then image data is generated based on the first scan data. This first image contains the image of the patient table. On the other hand, in a state in which the object is placed on the patient table, the patient table and the object are scanned to acquire the second scan data, and then image data is generated based on the second scan data. The second image contains the image of the patient table and the object. Moreover, based on the first image and the second image, the displacement of the patient table in a state in which the object is not placed on the patient table and the patient table in a state in which the object is placed on the patient table is calculated and the positions of the second image will be corrected.

As described above, according to the first aspect, because the effect of deflection from the patient table can be corrected based on the image of the patient table in a state in which the object is not placed on the patient table and the image of the patient table in a state in which the object has been placed on the patient table, unlike the conventional method, the effect of deflection from the patient table can be corrected without significantly altering the device.

In a second aspect of the invention, a medical image diagnosis apparatus comprising: a patient table; a patient table drive configured to move the patient table in a specified patient table moving direction; a data acquisition part configured to scan the patient table in a non-loaded state in which an object is not placed on the patient table to acquire first scan data for each of a plurality of positions in the specified patient table moving direction and to scan the patient table and the object in a loaded state in which the object is placed on the patient table to acquire second scan data for each of the plurality of positions; an image data-forming part configured to form a first tomographic image based on the first scan data and forms a second tomographic image based on the second scan data, for each of the plurality of positions; a displacement calculation part configured to calculate displacement of the patient table in the non-loaded state and in the loaded state based on the first tomographic image and the second tomographic image for each of the plurality of positions; and a tilt angle calculation part configured to calculate the tilt angle made by a cross-section of the first tomographic image and a cross-section of the second tomographic image at each of the plurality of positions based on the displacement; wherein the image data-forming part forms the tomographic image of the object for the cross-section of the first tomographic image based on the tilt angle for each of the plurality of positions.

According to the second aspect, a tomographic image (first tomographic image) in a state in which the object is not placed on the patient table and a tomographic image (second tomographic image) in a state in which the object is placed on the patient table will be generated for each of the multiple positions of the patient table moving direction and the displacement of the patient table in the tomographic image in a state in which the object is not placed on the patient table and the patient table in a state in which the object is placed on the table. Moreover, the tilt angle of the cross-section of the tomographic image in a state in which the object is not placed on the patient table and the cross-section of the tomographic image in a state in which the object is placed on the patient table is calculated for each of the multiple positions. Then, based on the tilt angle, the tomographic image of the object for the cross-section of the tomographic image in a state in which the object is not placed on the patient table will be generated for each of the multiple positions.

As described above, according to the second aspect, because the effect of deflection from the patient table (tilt of tomographic images) can be corrected based on the image of the patient table in a state in which the object is not placed on the patient table and the image of the patient table in a state in which the object has been placed on the patient table, unlike the conventional method, the effect of deflection from the patient table can be corrected without significantly altering the device.

In a third aspect of the invention, a control method for a medical image diagnosis apparatus including: a patient table; a data acquisition part configured to scan an object placed on the patient table to acquire scan data; an image data-forming part configured to form the image based on the scan data; and an image data processing part configured to process the image; the control method comprising: in a non-loaded state in which an object is not placed on the patient table, controlling the data acquisition part to scan the patient table to acquire first scan data, and controlling the image data-forming part to form a first image based on the first scan data, and in a loaded state in which an object is placed on the patient table, controlling the data acquisition part to scan the patient table and the object to acquire second scan data, and controlling the image data-forming part to form a second image based on the second scan data, and controlling the image data processing part to calculate displacement of the patient table in the non-loaded state and in the loaded state based on the first image and second image and to correct the position of the second image based on the displacement.

According to the third aspect, the scanning takes place for both the state in which the object is not placed on the patient table and the state in which the object is placed on the patient table. In a state in which the object is not placed on the patient table, the patient table is scanned to acquire the first scan data, and then image data is generated based on the first scan data. This first image contains the image of the patient table. On the other hand, in a state in which the object is placed on the patient table, the patient table and the object are scanned to acquire the second scan data, and then image data is generated based on the second scan data. The second image contains the image of the patient table and the object. Moreover, based on the first image and the second image, the displacement of the patient table in a state in which the object is not placed on the patient table and the patient table in a state in which the object is placed on the patient table is calculated and the positions of the second image will be corrected.

As described above, according to the third aspect, because the effect of deflection from the patient table can be corrected based on the image of the patient table in a state in which the object is not placed on the patient table and the image of the patient table in a state in which the object has been placed on the patient table, unlike the conventional method, the effect of deflection from the patient table can be corrected without significantly altering the device.

In a fourth aspect of the invention, a control method for medical image diagnosis apparatus including: a patient table; a patient table drive configured to move the patient table to a specified patient table moving direction; a data acquisition part configured to scan an object placed on the patient table to acquire scan data; an image data-forming part configured to form an image based on the scan data; and an image data processing part configured to process the image, the control method comprising: in a non-loaded state in which an object is not placed on the patient table, controlling the data acquisition part to scan the patient table to acquire first scan data for each of the plurality of positions of the specified patient table moving directions, and controlling the image data-forming part to form a first tomographic image based on the first scan data for each of the plurality of positions, and in a loaded state in which an object is placed on the patient table, controlling the data acquisition part to scan the patient table and the object to acquire second scan data for each of the plurality of positions, and controlling the image data-forming part to form a second tomographic image based on the second scan data for each of the plurality of positions, and controlling the image data processing part to calculate displacement of the patient table in the non-loaded state and in the loaded state based on the first tomographic image and the second tomographic image for each of the plurality of positions and to calculate a tilt angle formed by a cross-section of the first tomographic image and a cross-section of the second tomographic image for each of the plurality of positions based on the displacement, and controlling the image data-forming part to form the tomographic image of the object in the cross-section of the first tomographic image based on the tilt angle for each of the plurality of positions.

According to the fourth aspect, the scanning takes place for both the state in which the object is not placed on the patient table and the state in which the object is placed on the patient table. In a state in which the object is not placed on the patient table, the patient table is scanned to acquire the first scan data, and then image data is generated based on the first scan data. This first image contains the image of the patient table. On the other hand, in a state in which the object is placed on the patient table, the patient table and the object are scanned to acquire the second scan data, and then image data is generated based on the second scan data. The second image contains the image of the patient table and the object. Moreover, based on the first image and the second image, the displacement of the patient table in a state in which the object is not placed on the patient table and the patient table in a state in which the object is placed on the patient table is calculated and the positions of the second image will be corrected.

As described above, according to the fourth aspect, because the effect of deflection from the patient table (tilt of tomographic images) can be corrected based on the image of the patient table in a state in which the object is not placed on the patient table and the image of the patient table in a state in which the object has been placed on the patient table, unlike the conventional method, the effect of deflection from the patient table can be corrected without significantly altering the device.

DETAILED DESCRIPTION OF THE PREFERRED EMBODIMENTS

Embodiments of the medical image diagnosis apparatus and control method thereof related to the invention is described in detail with reference to the accompanying drawings. In this embodiment, the construction parts similar to the explained configuration will be described with the same symbols shown in FIG. 1 and FIG. 2.

An X-ray CT apparatus in connection with the construction of this invention will be described in the following embodiment, where the construction related to this invention can be applied to any medical image diagnosis apparatus (e.g., an X-ray diagnostic apparatus, nuclear medical diagnosis apparatus, MRI apparatus, etc.) to which the patient table bends by the weight of the object.

Device Construction

Figure 1:
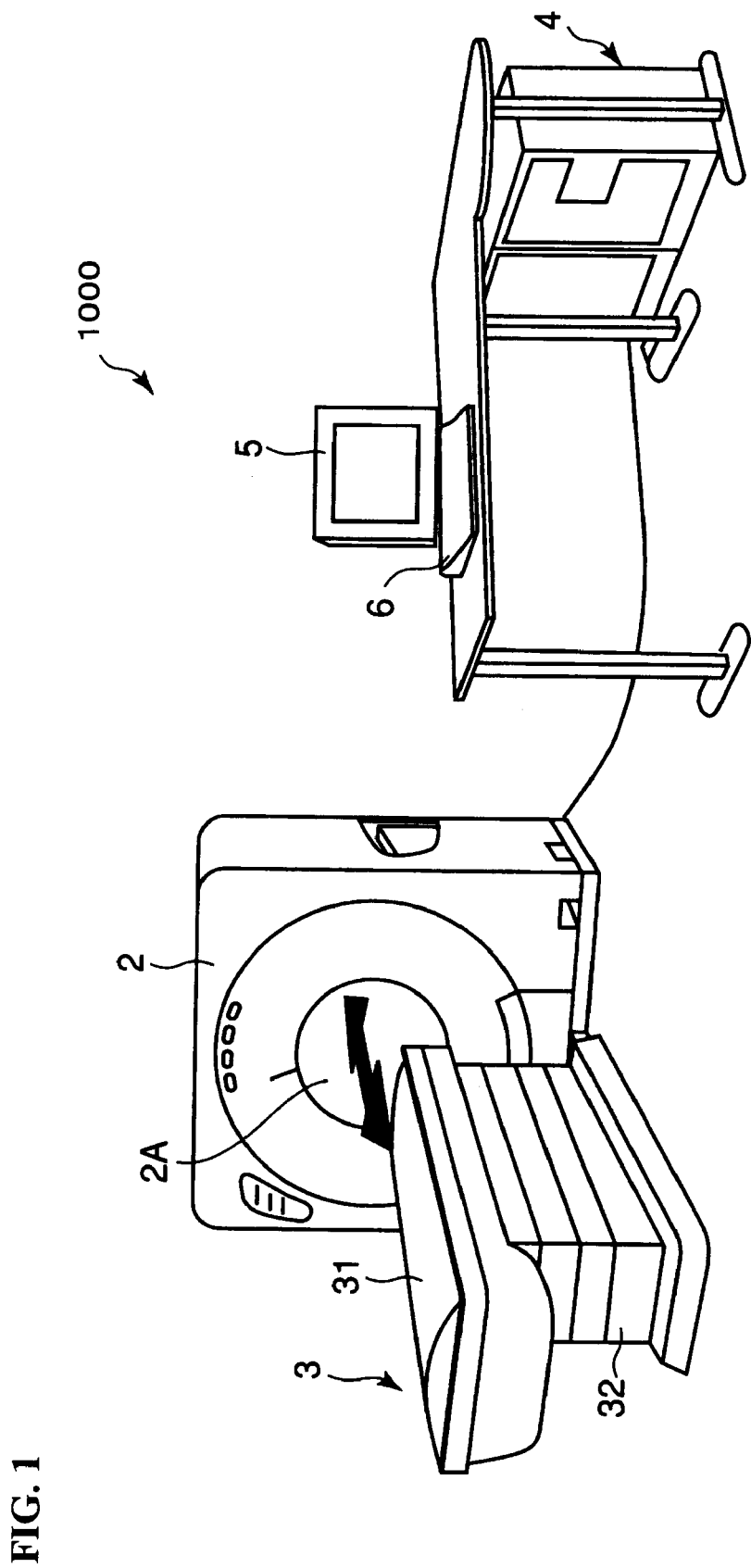
FIG. 1 is a schematic perspective view showing an example of the appearance of the composition of a conventional medical image diagnosis apparatus (X-ray CT apparatus).
Figure 5:
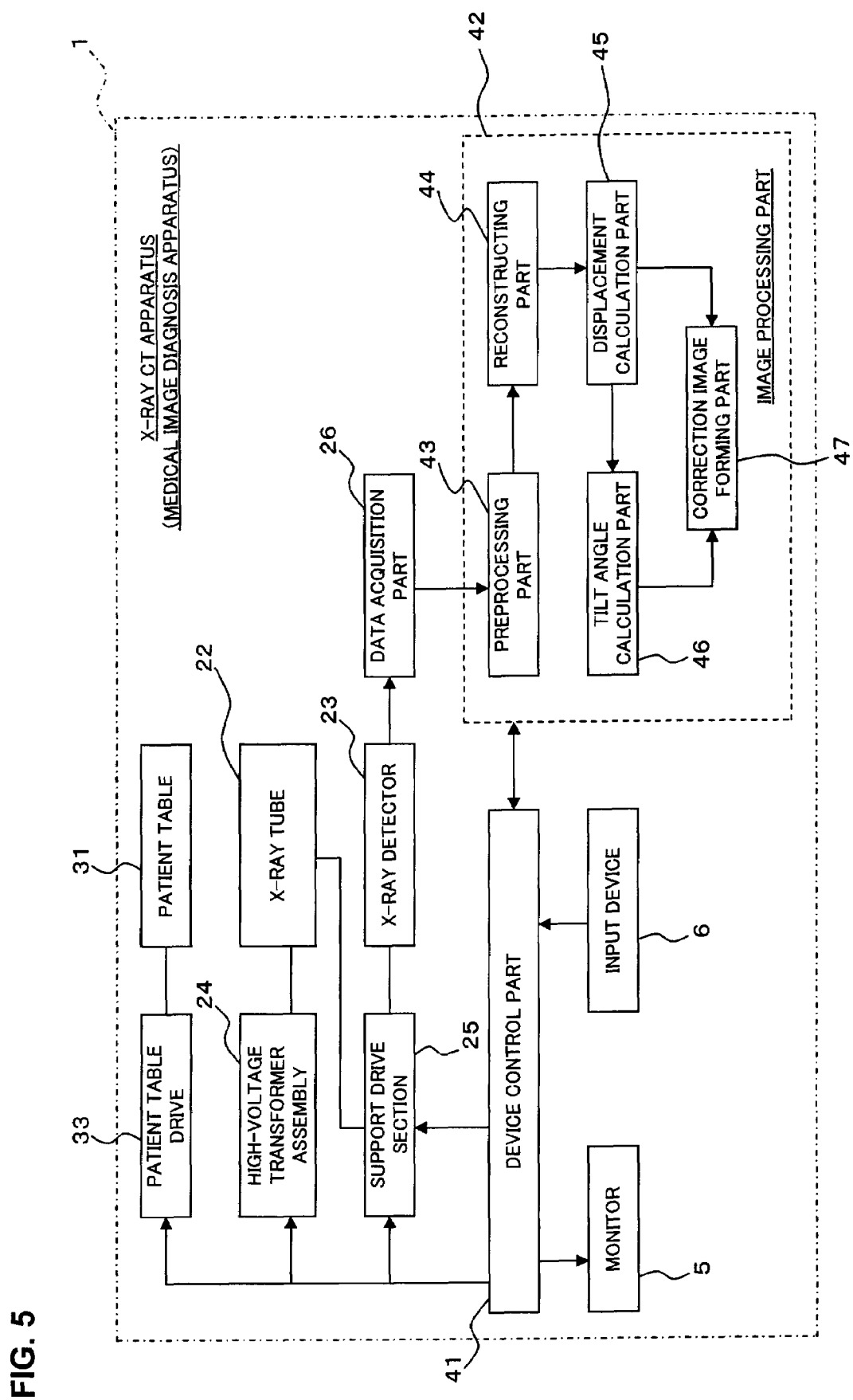
FIG. 5 is a schematic block diagram showing an example of the composition of the preferred embodiment of the image diagnosis apparatus (X-ray CT apparatus) related to the invention.
Figure 6:
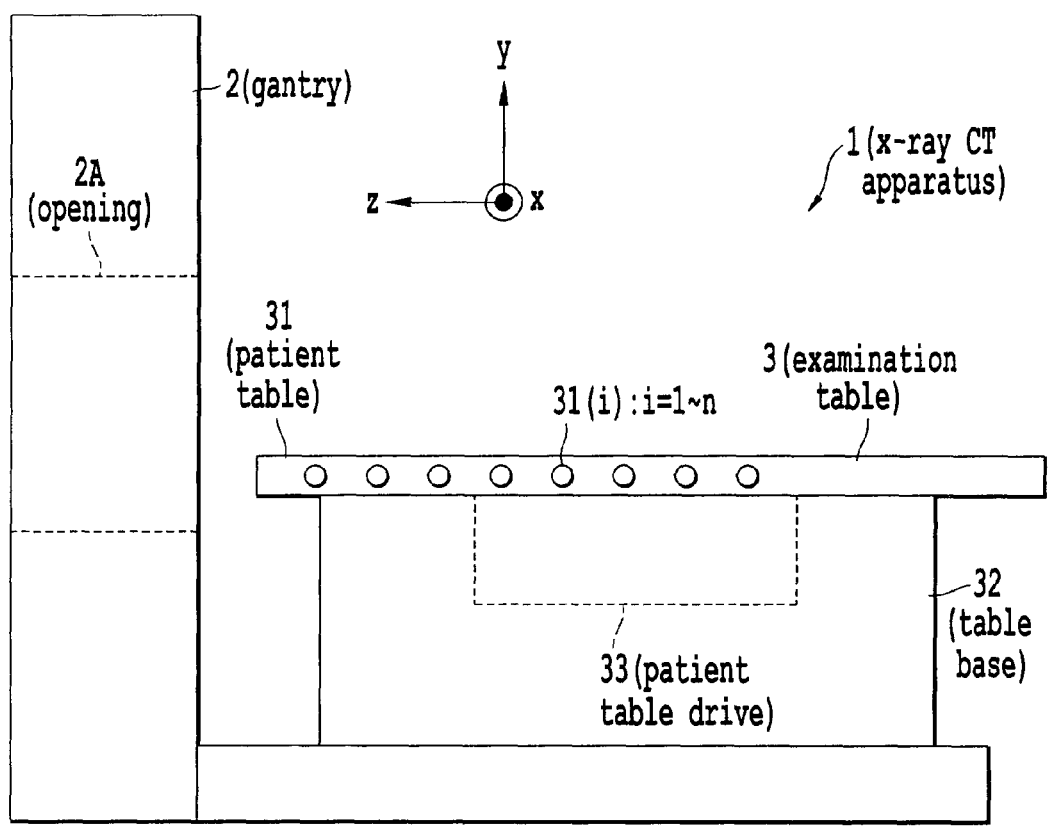
FIG. 6 is a schematic side-view showing an example of the composition of the preferred embodiment of the image diagnosis apparatus (X-ray CT apparatus) related to the invention.

FIG. 5 and FIG. 6 show an example of the construction of the X-ray CT apparatus (medical image diagnosis apparatus) related to the embodiment. This X-ray CT apparatus 1 has the similar view as the conventional ones and comprises a gantry 2, examination table 3, computer 4, monitor 5 and input device 6 as shown in FIG. 1. The monitor 5 and input device 6 are used as a console for the X-ray CT apparatus 1.

The examination table 3 comprises a patient table 31 and an examination table base 32 as shown in FIG. 6 and FIG. 1. The examination table base 32 houses the patient table drive 33 that moves the patient table 31 in an anteroposterior direction (z-direction), up and down direction (y-direction), and longitudinal direction (x-direction) respectively. The z-direction is explained as an example of "the specified patient table moving direction" of this invention.

A plurality (n) of markers 31 (1) to 31 (n) are provided on the side of the patient table 31 as shown in FIG. 6. These markers 31 (i) (i=1 to n), for example, are provided evenly spaced apart (let d=the space between the adjacent markers). Each marker 31 (i) is used as an example to show the "reference position" of this invention. Each marker 31 (i), for example, is formed with material having a different X-ray absorption from that of the patient table 31.

Figure 2:
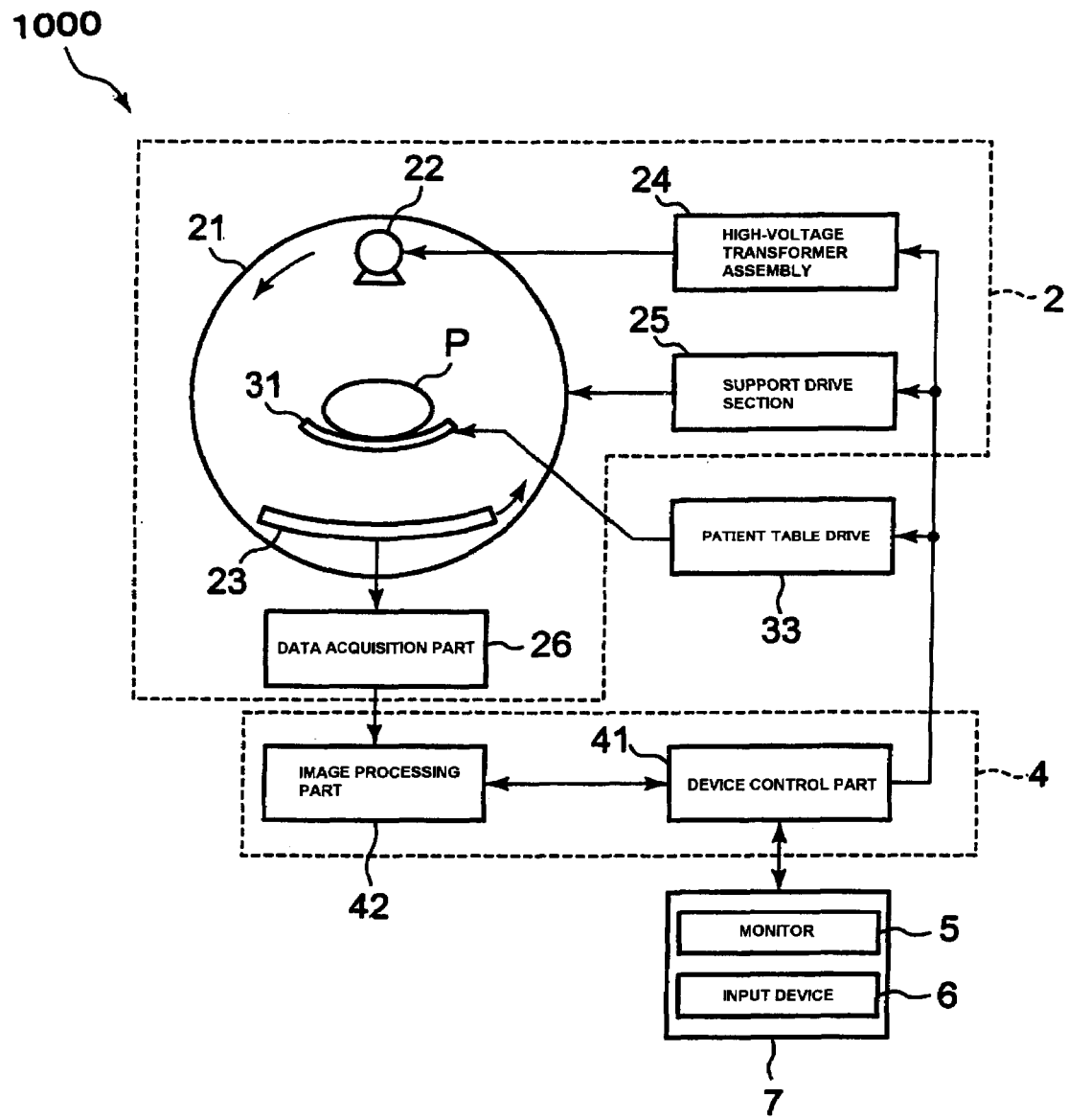
FIG. 2 is a schematic diagram showing an example of the composition of a conventional medical image diagnosis apparatus (X-ray CT apparatus).

The gantry 2 houses a support 21 that supports the X-ray tube 22 and X-ray detector 23 as shown in FIG. 2. The X-ray tube 22 radiates X-ray based on high voltage having specified tube voltage and tube current applied by a high-voltage transformer assembly 24 shown in FIG. 5, and is explained as an example of the "X-ray generator" of this invention.

The X-ray detector 23, supported at the location opposite to the X-ray tube 22 over the opening 2A of the gantry 2 as shown in FIG. 6 and FIG. 1, has arrayed multiple X-ray detection elements that detect X rays generated from the X-ray tube 22. The X-ray detector 23 is explained as an example of the "X-ray detector" of this invention.

The support drive section 25 rotates the support 21 along the circumference of the opening 2A. By this, the X-ray tube 22 and X-ray detector 23 rotate along the circumference of the opening 2A in an unified manner to scan the object P with X-ray beams from various directions. The X-ray detector 23 detects the X-ray beams that have transmitted the object P and patient table 31 and delivers the data of the transmitted X-ray dosage to the data acquisition part 26. Furthermore, the support drive section 25 executes the operation that tilts the support 21 to the object P (patient table 31). The support drive section 25 functions as an example of "rotary drive" of this invention.

The data acquisition part 26, comprising DAS having arrayed multiple data acquisition elements corresponding to the X-ray detection element of the X-ray detector 23, so as to collect data of the transmitted X-ray dosage delivered from the X-ray detector 23. The data acquisition part 26 performs amplification and A/D conversion processing of the collected data to transmit the data to the computer 4.

The gantry 2 acquires data of the X-ray dosage (scan data) that transmitted the object P and patient table 31 by executing the above mentioned operation. The gantry 2 functions as an example of "data acquisition part" of this invention.

The computer 4 comprises the same construction as a general computer. In other words, the computer 4 comprises a microprocessor, RAM, ROM, a hard disk drive and data communication interface etc (not shown here).

The storage device including a hard disk drive and ROM etc. houses a control program not shown in advance. The microprocessor controls each part of the apparatus to control the X-ray CT apparatus 1 to execute the operations related to this invention according to the control program.

The computer 4 comprises a device control part 41 and image processing part 42. The device control part 41 controls the operations of the each part of the X-ray CT apparatus 1, including the high-voltage transformer assembly 24, support drive section 25, patient table drive 33 and monitor 5, etc. The device control part 41 comprises, for example, a microprocessor, etc. The device control part 41 functions as an example of the "scan controller" of this invention.

Particularly, the device control part 41 controls the patient table drive 33 to change the part of the object P that is positioned at the intermediate position between X-ray tube 22 and X-ray detector 23 (in other words, to change the part of the object P to be X-ray scanned). In addition, the device control part 41 controls the support drive section 25 to rotate the X-ray tube 22 and X-ray detector 23 in an unified manner to perform X-ray scan the object P and patient table 31 from various directions.

Furthermore, the device control part 41 simultaneously controls the patient table drive 33 and support drive section 25 to perform a helical scan. Helical scan is a scanning method of an X-ray scanning by constantly moving the patient table 31 so as to form a spiral trajectory of the X-ray tube 22 (X-ray detector 23) toward the object P and patient table 31.

The image processing part 42 performs a processing of forming (image data of) an image of the object P and patient table 31 and various image processing of the image data. This image processing part 42 comprises a preprocessing part 43, reconstructing part 44, displacement calculation part 45, tilt angle calculation part 46 and correction image forming part 47.

The preprocessing part 43 performs a processing of generating projection data provided for reconstruction of the image. Specifically, the preprocessing part 43 performs a series of processing called preprocessing, including logarithmic data transformation, reference correction, water calibration beam hardening correction and motion correction for data sent from the data acquisition part 26 of the gantry to generate projection data. The preprocessing part 43 comprises, for example, a circuit board and a microprocessor, etc., that execute these preprocessing.

The reconstructing part 44 performs a processing using image reconstruction method for projection data generated from the preprocessing part 43 to generate image data of the tomographic image of the object P and patient table 31. The image reconstruction method being used includes some known methods such as convolution back projection method, divergent ray convolution back projection method, two-dimensional Fourier transformation method, etc.

Herein, when performing a helical scan, an image constructing method with interpolation processing of image, for example, 360° interpolation method, 180° interpolation method, 180° extrapolation method, opposite ray interpolation method, filter method, is applied. The reconstructing part 44 comprises, for example, a circuit board and microprocessors, etc., that execute the reconstruction process by the above mentioned image reconstruction method.

Here, the image processing part 42 (computer 4) including the preprocessing part 43 and reconstructing part 44 functions as an example of the "image data producing part" of this invention.

The displacement calculation part 45 performs a processing of calculating displacement between the position of the patient table 31 in an up-and-down direction (y-direction) formed in a non-loaded state and the position of the tabletop 31 in a loaded state. In the non-loaded state, the object P is not placed on the patient table. In the loaded state, the object P is placed on the patient table. The computing process is executed based on the each image data of the image including the image of the patient table 31 acquired in both the non-loaded state and the loaded state. The detail about the computing process will be described hereinafter. The displacement calculation part 45 comprises microprocessor, etc., that execute the computing process. The displacement calculation part 45 functions as an example of the "displacement calculation part" of this invention.

The tilt angle calculation part 46 performs a processing of calculating the tilt angle of a tomographic image (axial image) of the patient table 31 in the non-loaded state and a tomographic image (axial image) of the patient table 31 (object P) in the loaded state based on the displacement calculated by the displacement calculation part 45. The details of the computing process will be described hereinafter. The tilt angle calculation part 46 comprises a microprocessor, etc., that execute the computing process. The tilt angle calculation part 46 functions as an example of the "tilt angle computing method" of this invention.

The correction image forming part 47 performs a processing of correcting the position of the image data of the object P and patient table 31 corresponding to the up-and-down direction (y-direction) based on the displacement calculated by the displacement calculation part. The details of the correction process will be described hereinafter. The correction image forming part 47 functions as an example of the "correction part" of this invention by performing such an image position correction process.

Here, the direction corresponding to the y-direction means the direction in the image data corresponding to the y-direction in real space. For example, said corresponding direction in axial image will be upward direction of the image. Said direction may simply be referred to as "y-direction" by equating the direction in real space with the direction in image data.

Meanwhile, the correction image forming part 47 performs a processing of forming image data of a tomographic image with the tilt angle corrected by the tilt angle calculated by the tilt angle calculation part 46. The details of the processing will be described hereinafter. The correction image forming part 47 functions as an example of the "image data producing part" of the invention by performing such correction image forming processing.

Here, the device control part 41 and (the computer 4 comprising) the image processing part 42 function as an example of the "computer" of this invention. In addition, the image-processing part that includes the 42 displacement calculation part 45, tilt angle calculation part 46 and correction image forming part 47 functions as an example of "image data processing part" of this invention.

First Type of Usage

Figure 7:
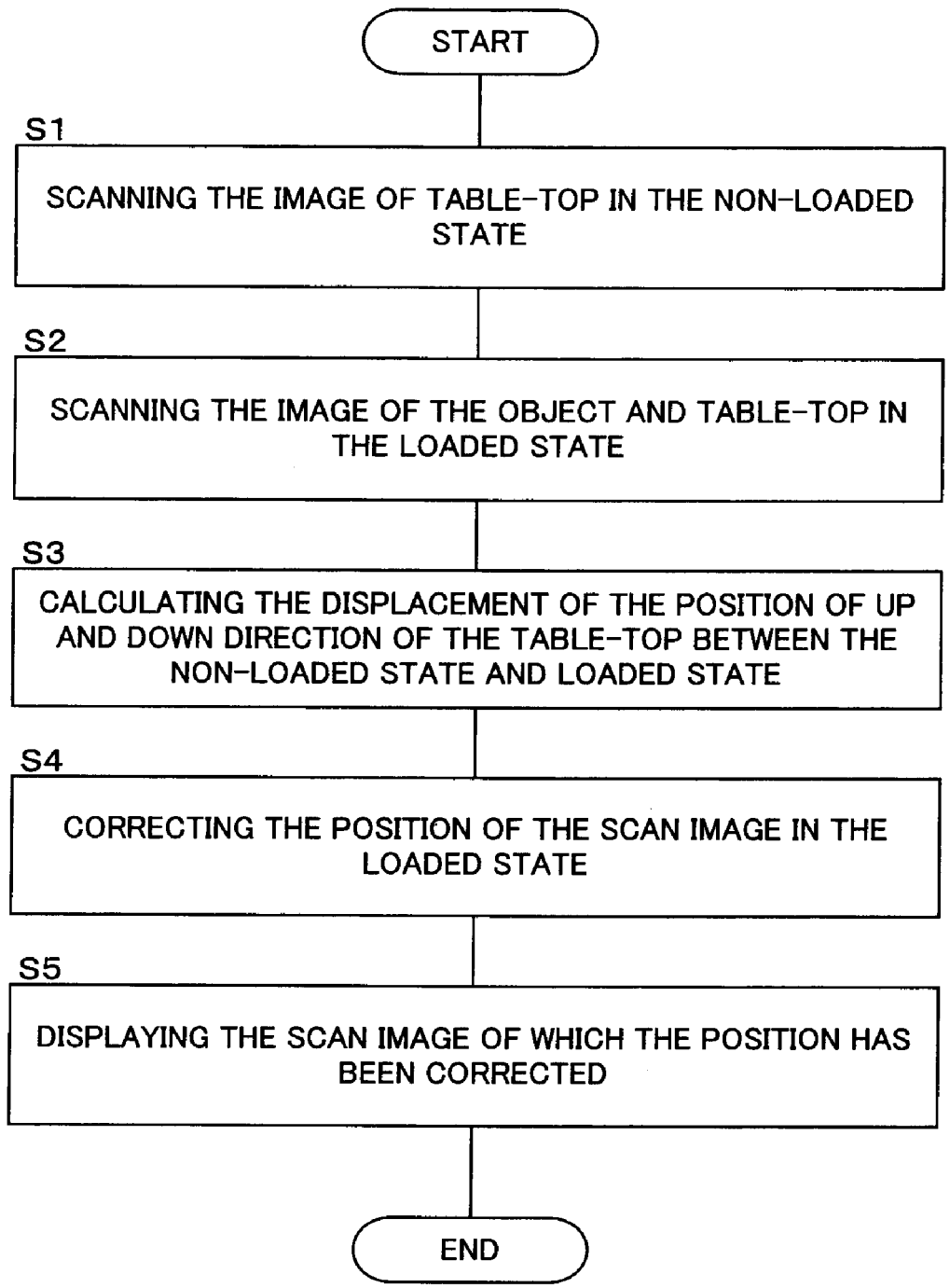
FIG. 7 is a flow chart showing an example of the preferred embodiment using the image diagnosis apparatus (X-ray CT apparatus) related to the invention.

Now, the embodiment using the X-ray CT apparatus 1 comprising the above mentioned construction is described hereinafter. The flowchart shown in FIG. 7 illustrates an example of the embodiment using the X-ray CT apparatus 1 (first type of usage). The first type of usage is about correcting displacement of the image of the object P in an up-and-down direction (y-direction).

First, summary of the used embodiment shown in the flowchart in FIG. 7 is described, and then, details of the operation of the X-ray CT apparatus 1 at each step of said used embodiment will be described.

Summary of the First Type of Usage

To begin with, an image of the patient table 31 is acquired in a non-loaded state in which the object P is not placed on the patient table (S1). This acquired image consists of the image of the patient table 31 (here, it is a tomographic image with its cross-section as xy-flat surface) and is explained as an example of the "first image" of this invention. This image data of the acquired image in the non-loaded state is, for example, stored in the above mentioned storage device such as a hard disk drive, etc.

Meanwhile, imaging in the non-loaded state may take place regularly, such as once a month, or only once when installing the X-ray CT apparatus 1, or each time when a CT image of the object P is taken. Note that in the case last mentioned, the patient table 31 may be scanned after the image of the object P is acquired.

Next, an image of the object P and patient table 3 will be scanned with the object P placed on the patient table 31(S2) This acquired image consists of the image of the object P and patient table 31 (a tomographic image with its cross-section as xy-flat surface) and is explained as an example of the "second image" of this invention. The tomographic image acquired in this step S2 is a tomographic image that is located in generally the same location as the tomographic image of the patient table 31. The image data of the acquired image in the loaded state is, for example, stored in the above mentioned storage device such as a hard disk drive.

Here, information including patient information of said object P and setting information at acquiring the image will be stored with the image data. Here, the patient information is various information related to said object P including patient ID, name and birth date. In addition, the setting information at acquiring an image includes information such as the setting value of tube voltage and tube current, setting value of slice location and slice interval that indicate the forming location of the tomographic image (axial image), helical pitch (the movement distance of the patient table 31 in a helical scan during the period the X-ray tube 22 and X-ray detector 23 rotate 360°) etc. This information is, for example, added to the image data as additional information of DICOM (Digital Imaging and Communications in Medicine).

Next, displacement calculation part 45 calculates displacement of the position of the y-direction (y-coordinate value) of the patient table 31 in the non-loaded state and the position of the y-direction (y-coordinate value) of the patient table 31 in the loaded state. This calculation is based on the image data of the acquired image in the non-loaded state and the image data of the acquired image in the loaded state (S3).

And then, the correction image forming part 47 corrects the position of the image data of the image acquired in step S2 in the y-direction based on the displacement of the patient table 31 in the y-direction calculated in step S3 (S4).

Lastly, the device control part 41 controls the monitor 5 to display an image based on the image data of which the position has been corrected (S5). Furthermore, it is possible to store the image data of which the location has been corrected in a storage device such as a hard disk drive, etc., or save it on a media (e.g., CD-R, DVD-RAM, etc.) by a drive device that is not shown here.

Details of the Operations for Each Step
(Step S1: Imaging in the Non-Loaded State)

Described hereinafter is about acquiring image of the patient table 31 in a state in which the object P is not placed on the patient table (step S1).

When a user conducts a prescribed start-up operation by using the input device 6, the device control part 41 controls the high-voltage transformer assembly 24 to control the X-ray tube 22 to radiate X-rays as well as controls the patient table drive 33 and support drive section 25 to perform X-ray scan at least the locations of each marker 31(i) of the patient table 31. The scanning method here may be helical scan or conventional scan (a method that scans X-ray beam patient table 31 while halting the patient table 31).

X-ray detector 23 successively detects the X-rays that have transmitted through the patient table 31 and sends the detected data to the data acquisition part 26. The data acquisition part 26 collects the detected data, performs a prescribed processing and then delivers it to the preprocessing part 43.

The preprocessing part 43 forms projection data based on the data received from the data acquisition part 26. The reconstructing part 44 forms image data including the tomographic image of the patient table 31 whose slice location is at least the location of each marker 31 (i). As a result, n-unit of image data of the tomographic image, whose slice location is at least the location of each marker 31 (1) to 31 (n) and cross-section is xy-flat surface, will be acquired. This image data is stored in a storage device such as a hard disk drive.

(Step S2: Imaging in the Loaded State)

Described hereinafter is about acquiring image of the patient table 31 in a state in which the object P is placed on the patient table (step S2).

When a user conducts a prescribed start-up operation, the device control part 41 controls the high-voltage transformer assembly 24 to control the X-ray tube 22 to radiate X-rays as well as controls the patient table drive 33 and support drive section 25 to perform X-ray scan at least the locations of each marker 31 (i) of the patient table 31. The scanning method here may be helical scan or conventional scan.

The data acquisition part 26 collects the detected data detected by X-ray detector 23, performs a prescribed processing and then delivers it to the preprocessing part 43.

The preprocessing part 43 forms projection data based on the data received from the data acquisition part 26. The reconstructing part 44 forms image data including the tomographic image of the object P and tomographic image of the patient table 31 whose slice location is at least the location of each marker 31 (i). As a result, n-unit of image data of the tomographic image, whose slice location is at least the location of the each marker 31 (1) to 31 (n) and cross-section is xy-flat surface, will be acquired. This image data is stored in a storage device such as a hard disk drive.

(Step S3: Computing Process for Displacement of the Patient Table)

Described hereinafter is regarding a process of computing displacement between the location of the patient table 31 in the y-direction in the non-loaded state and the location of the patient table 31 in the y-direction in the loaded state (step S3).

First, the displacement calculation part 45 reads the image data of a tomographic image at the location of the each marker 31 (i) that has been acquired in step S1 from the storage device. Then, it determines the location of the tomographic image of the tabletop 31 in said tomographic image in the y-direction based on each image data, in other words, the y-coordinate value (in the non-loaded state).

Similarly, displacement calculation part 45 reads the image data of a tomographic image at the location of each marker 31 (i) that has been acquired in step S2 from the storage device, and then it determines the y-coordinate value of the tomographic image of the patient table in said tomographic image based on each image data (in the loaded state).

Figure 8:
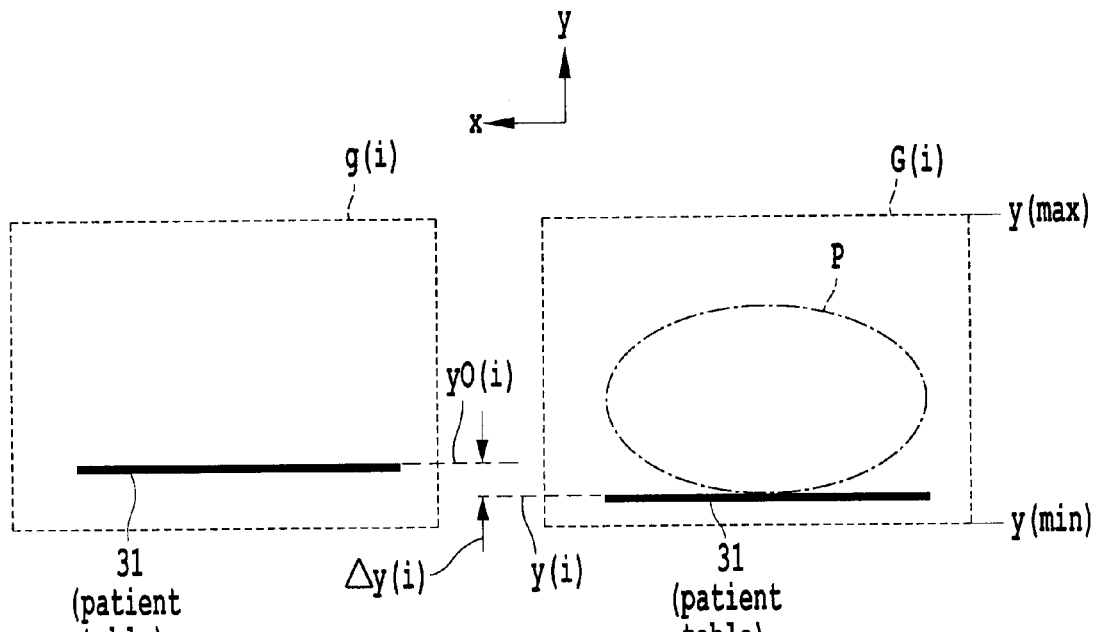
FIG. 8 is a schematic diagram explaining an example of the preferred embodiment using the image diagnosis apparatus (X-ray CT apparatus) related to the invention.

Such processing by the displacement calculation part 45 is described hereinafter with reference to FIG. 8. Here, the tomographic image acquired in the location of the markers 31 (i) in the non-loaded state is indicated as a symbol g (i), and the tomographic image acquired in the location of the markers 31 (i) in the loaded state is indicated as a symbol G (i).

The scanned area (the area that forms an image) in the y-direction is preset for each of the tomographic images g (i) and G (i). In FIG. 8, the scanned area in the y-direction is y=y (min)–y (max) because the upward direction in real space (the upward direction in an image) is deemed to be +y-direction.

The displacement calculation part 45 analyzes the image data of the tomographic image g (i) and extracts (the image data of) the tomographic image of the patient table 31 from (the image data of) the tomographic image g (i). This processing can be executed, for example, by extracting the pixels having a CT number corresponding to the X-ray absorption of the patient table 31 or markers 31 (i). In addition, any extracting method can be applied, for example, memorizing the cross-section shape of the patient table 31 in advance, and then searching the cross-section shape corresponding to the image area from the tomographic image of the patient table 31, etc.

Furthermore, the displacement calculation part 45 determines the y-coordinate value y0 (i) of the extracted tomographic image of the patient table 31. This processing determines the distance to the upper end of the image (y-coordinate value y (max)) (pixel count) and to the lower end of the image (y-coordinate value y (min)) separately, from the prescribed location of the tomographic image of the patient table 31 (e.g., the image location corresponding to the distinctive locations of the patient table 31, such as the center, undersurface, or uppersurface, etc.), and further easily determines the y-coordinate value based on the ratio of these distances and the y-coordinate value y (max), y (min). When the y-coordinate is defined for (the image data of) the tomographic image g (i), the y-coordinate value at the prescribed location of the tomographic image of the patient table 31 can be directly determined.

The y-coordinate value y (i) of the tomographic image of the patient table 31 in the loaded state can also be determined by the same method as in the non-loaded state.

The displacement calculation part 45 calculates the difference between the y-coordinate value y0 (i) and y (i) of the tomographic image of the patient table 31 determined as such for each marker 31 (i) in the non-loaded state and in the loaded state: $\Delta y = y(i) - y0(i)$. Here, $\Delta y \leq 0$ because upward direction is defined as +y-direction. This $\Delta y$ indicates the displacement of the height of the patient table 31 in the loaded state in relation to the height of the patient table 31 (vertical position) in the non-loaded state.

(Step S4: Location Correction of an Image)

Figure 9:
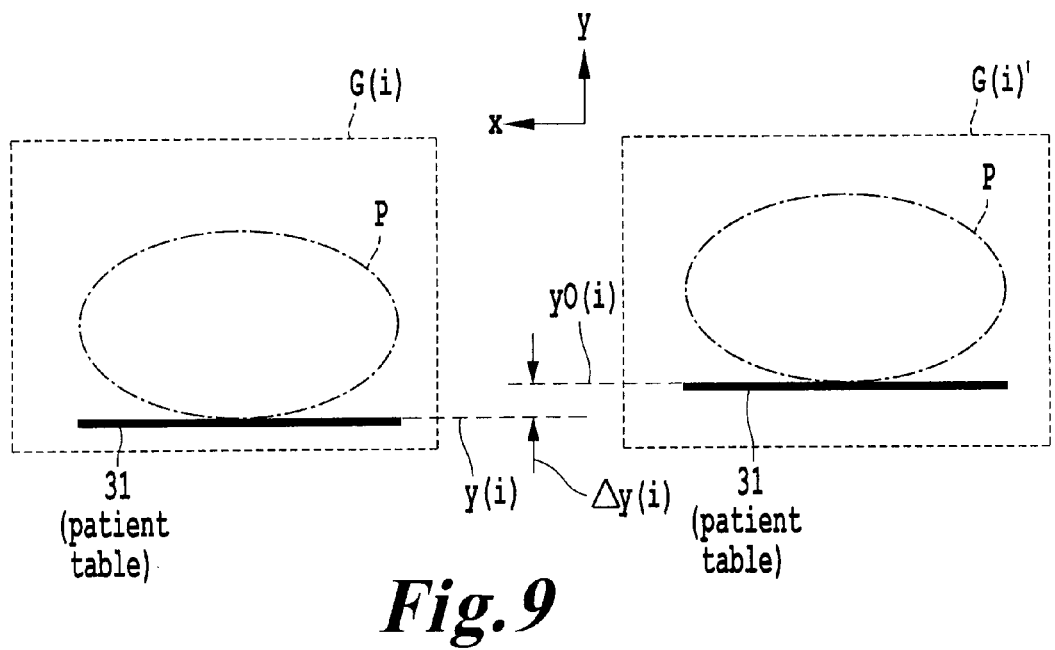
FIG. 9 is a schematic diagram explaining an example of the preferred embodiment using the image diagnosis apparatus (X-ray CT apparatus) related to the invention.

The processing of correcting the location of image data of a tomographic image of the object P (and patient table 31) in the y-direction that has been acquired in step S2 is described hereinafter with reference with FIG. 9 (step S4).

The correction image forming part 47 extracts a tomographic image of the object P in the tomographic image G (i) based on the image data of a tomographic image G (i) at the location of the each marker 31 (i). This processing can be executed by, for example, performing a threshold processing regarding the CT number based on the X-ray absorption of the tissue of the human body. To give an actual example, the range of the CT number based on the X-ray absorption of the skin of the human body is presented, and then the pixels having the CT number included in the range is extracted. As a result, the image area corresponding to the skin will be extracted. This image area outlines the tomographic image of the object P, so the image area surrounded by the outline is extracted as image corresponding to the tomographic image of the object P. Here, the tomographic image of the patient table 31 may also be extracted by using the above mentioned manner.

Furthermore, the correction image forming part 47 forms the image data of the tomographic image G (i)', which is the tomographic image of the object P (and the tomographic image of the patient table 31) that has been moved in the y-direction, based on the displacement $\Delta y$ (i) corresponding to the location of said markers 31 (i) calculated in step S4. To obtain the tomographic image G (i)', the tomographic image of the object P (and the tomographic image of the patient table 31) in the tomographic image G (i)' is moved in upward direction compared to the tomographic image G (i) that is before correction. In other words, this correction causes the tomographic image of the object P to move to the image location when the patient table 31 is located at the level of a state in which the object is not placed on the table.

The device control part 41 controls the monitor 5 to display the tomographic image G (i)' (step S5).

(Effects and Advantages of the First Type of Usage)

According to the first type of usage of such X-ray CT apparatus 1, since the patient table 31 in the non-loaded state is scanned separately to compare the location of the image of the patient table 31 in the non-loaded state with the location of the image of the patient table 31 in the loaded state, the downward displacement of the reconstructed image caused by the deflection from the patient table 31 by the weight of the object P can be corrected.

Therefore, according to the first type of usage, effect of the deflection from the patient table 31 can be corrected without performing a major alteration to the hardware configuration of the apparatus such as adding a new device of system to an X-ray CT apparatus (medical image diagnosis apparatus) with a general construction.

In addition, because the first type of usage is different from the invention described in Japanese Unexamined Patent Application Publication No. 2004-180846, which corrects the effect of deflection from the patient table 31 by tilting the patient table 31 of gantry 2, there is no need to execute a complex control to successively change the angle of tilting the patient table 31 or gantry 2 in accordance with the change in tilt angle of the patient table 31. Therefore, the effect of deflection from the patient table 31 can be corrected more easily and very precisely than the invention in the document.

Furthermore, because the tilt angle of the object P placed on the patient table 31 is not changed in the first type of usage, the object P will never feel discomfort as in the case of the invention of Japanese Unexamined Patent Application Publication No. 2004-180846.

In addition, according to the first type of usage, because it is comprised to actually acquire an image of the patient table 31 for both in the non-loaded state and in the loaded state to compare their vertical positions to correct the displacement of the reconstructed image of the object P in an up-and-down direction, the displacement can be corrected with a high degree of accuracy.

Therefore, in particular, the first type of usage can be used preferably for treatment planning for radiation therapy. That is to say, considering the fact that the treatment planning is conducted by observing the reconstructed image of the object P to specify the X-ray irradiated site such as a tumor (the location of a tumor, etc.) and by marking said specified location of the object P which is placed horizontally on the patient table 31, etc., and that the reconstructed image of the first type of usage is corrected in accordance with the location of the patient table 31 in the non-loaded state which is generally horizontal, the corrected reconstructed image expresses the body position of the object P with high accuracy when the object is placed horizontally.

Therefore, the X-ray irradiated site specified from the reconstructed image and the actual location of the object P corresponding to the specified location can be associated with a high degree of accuracy, and the location irradiated can be decided as well with high accuracy. Accordingly, radiation can be accurately delivered to a tumor, etc., in radiation therapy, unnecessary radiation exposure to the object P can be reduced and the treatment effect can be improved.

Modified Embodiments of the First Type of Usage

Described hereinafter are modified embodiments of the first type of usage of the X-ray CT apparatus 1.

Modified Embodiment 1

According to the above mentioned first type of usage, markers 31 (i) are provided at the location for determining the displacement of the patient table 31 (reference position) in vertical direction to indicate the reference position. Instead of providing such markers 31 (*i*), distinctive positions of the patient table 31 may be set to reference positions to determine the displacement of the patient table 31.

For example, the edge of the patient table 31 near the gantry 2 may be the reference position. In that case, for example, the patient table 31 in the non-loaded state is assumed to be horizontal (in other words, the y-coordinate value of the patient table 31 at any location is assumed to be equal to the y-coordinate value of said edge).

Furthermore, for a tomographic image at any slice location in the loaded state, the y-coordinate value of the image of the patient table 31 in the tomographic image is determined to calculate the displacement of the y-coordinate value and the y-coordinate value of said edge. Then, the image of the object P in the tomographic image is displaced in the y-direction to perform a correction to offset the displacement.

Therefore, same as the above mentioned first type of usage, the effect of the patient table deflection can be corrected without a major alteration to the construction. In addition, treatment of a radiation therapy can be preferably planed. Here, although the patient table 31 in the non-loaded state is assumed to be horizontal, the accuracy of treatment planning is not lowered. The reason is that the object P is placed on the patient table 31 in a horizontal state in treatment planning.

In addition, such an assumption is not necessary for the same correction as the first type of usage. For example, when setting the edge of the patient table 31 as reference position, an image of the various locations including the reference position edge is acquired for both the non-loaded state and the loaded state. Furthermore, by referring to the relative distance (distance in the z-direction) from said reference position, the slice location of the image in the non-loaded state and the slice location of the image in the loaded state can be associated together. Then, the displacement of the image of the patient table 31 is calculated for both images at the associated slice location, so as to correct the location of the image of the object P at said slice location.

Modified Embodiment 2

In the above mentioned first type of usage, the markers 31 (*i*) are provided at the reference position that determines the displacement of the patient table 31 in vertical direction to determine the displacement of the image position of the patient table 31 in the non-loaded state and the position of the patient table 31 in the loaded state for each reference position, and correct the vertical position of the image of the object P at this reference position.

This modified embodiment 2 describes a construction that corrects the position of the image of the object P at locations other than prescribed reference position.

In the modified embodiment 2, the displacement calculation part 45, similar to the first type of usage, firstly acquires the location of the tomographic image g (i) of the patient table 31 $y0$ (*i*) acquired in the non-loaded state and the location of the tomographic image G (i) of the patient table 31 $y$ (*i*) acquired in the loaded state at the reference position indicated by each marker 31 (*i*). Then, the displacement calculation part 45 calculates the difference of these positions between $y0$ (*i*) and y (i) to determine the displacement $\Delta y$ (i) in up and down direction (y-direction) at said reference position.

Furthermore, the displacement calculation part 45 calculates the displacement $\Delta y$ ($\zeta$) at any position between the two reference positions (z-coordinate value=$\zeta$) based on the displacement $\Delta y$ (i), $\Delta y$ (i+1), which are calculated for both of the two reference positions (z-coordinate value=z (i), z (i+1)) indicated by the adjacent two markers 31 (*i*), 31 (*i*+1) (i=1–n−1).

The example of computing process of the displacement $\Delta y$ ($\zeta$) at any location z=$\zeta$ between the two reference positions z (i) and z (i+1) is specifically described hereinafter. As a first example, considerably many reference positions (markers 31(*i*)) are provided to considerably shorten the space between the adjacent reference positions z (i) and z(i+1). Then, the equation of the straight line connecting the locations indicated as coordinate value (y(i), z(i)) and (y(i+1), z(i+1)) (the location of the patient table 31) on yz-flat surface (the equation of the straight line connecting two points can easily be determined) is calculated. Then, z=$\zeta$ is substituted for the equation of the straight line, and the y value is calculated at this time to determine the displacement $\Delta y(\zeta)$ at the location z=$\zeta$.

According to the first example, without a major alteration to the construction, the effect of the patient table deflection from the patient table 31 at any location can be corrected.

In addition, the number (space) of the reference position laid in this example can be decided, for example, by measuring the degree of the displacement caused by its own weight of the patient table 31 in advance and approximating the displacement status (generally it bents in a curved line) between the adjacent reference positions to the straight line with desired accuracy. As a result, the correction of the patient table 31 at any location can be performed with high accuracy.

As the second example of processing of calculating the displacement $\Delta y(\zeta)$, based on the displacement $\Delta y(i)$ determined for each reference position z(i), the optimal curve line passing through the n-unit of locations (y(i), z(i)) is calculated among the curve lines defined on the yz-flat surface. This computing processing can be performed by using any curve fitting algorithm. This optimal curve line does not need to pass through all the n-unit of locations, and may be a curve line passing near the locations at least. In other words, for this optimal curve line, a curve line approximating the n-unit of locations, such as a curve line approximating a broken line connecting the n-unit of locations, is sufficient.

According to the second example, the effect of the patient table deflection from the patient table 31 at any location can be corrected without implementing a major alteration to the construction. In addition, also in said example, the correction accuracy can be improved by having considerably many reference positions.

The above mentioned second modified embodiment can be made simple by applying a helical scan. That is to say, a helical scan is performed to the patient table 31 in the non-loaded state to determine the y-coordinate value of the patient table 31 at the many locations of the patient table 31 in the z-direction. At this time, for example, the y-coordinate value can be determined in a millimeter order. It allows the displacement status of the patient table 31 at any location in the z-direction to be grasped (narrow space allows the displacement status to be grasped as a nearly-curved line) (in other words, the displacement of the patient table 31 is acquired as a very fine broken line.)). This information allows to correct the location in the y-direction of the tomographic image of the object P acquired at any location z=$\zeta$ in the z-direction in the loaded state.

In addition, in case that the y-coordinate value of the patient table 31 at the location z=$\zeta$ in the non-loaded state has not been acquired, the displacement can be calculated by using the y-coordinate value acquired at the nearest location of the location z=$\zeta$, or the displacement can also be calculated by acquiring the y-coordinate value at the location z=$\zeta$ in the non-loaded state based on the y-coordinate value acquired at the two locations holding the location z=ζ in between.

Second Type of Usage

Figure 10:
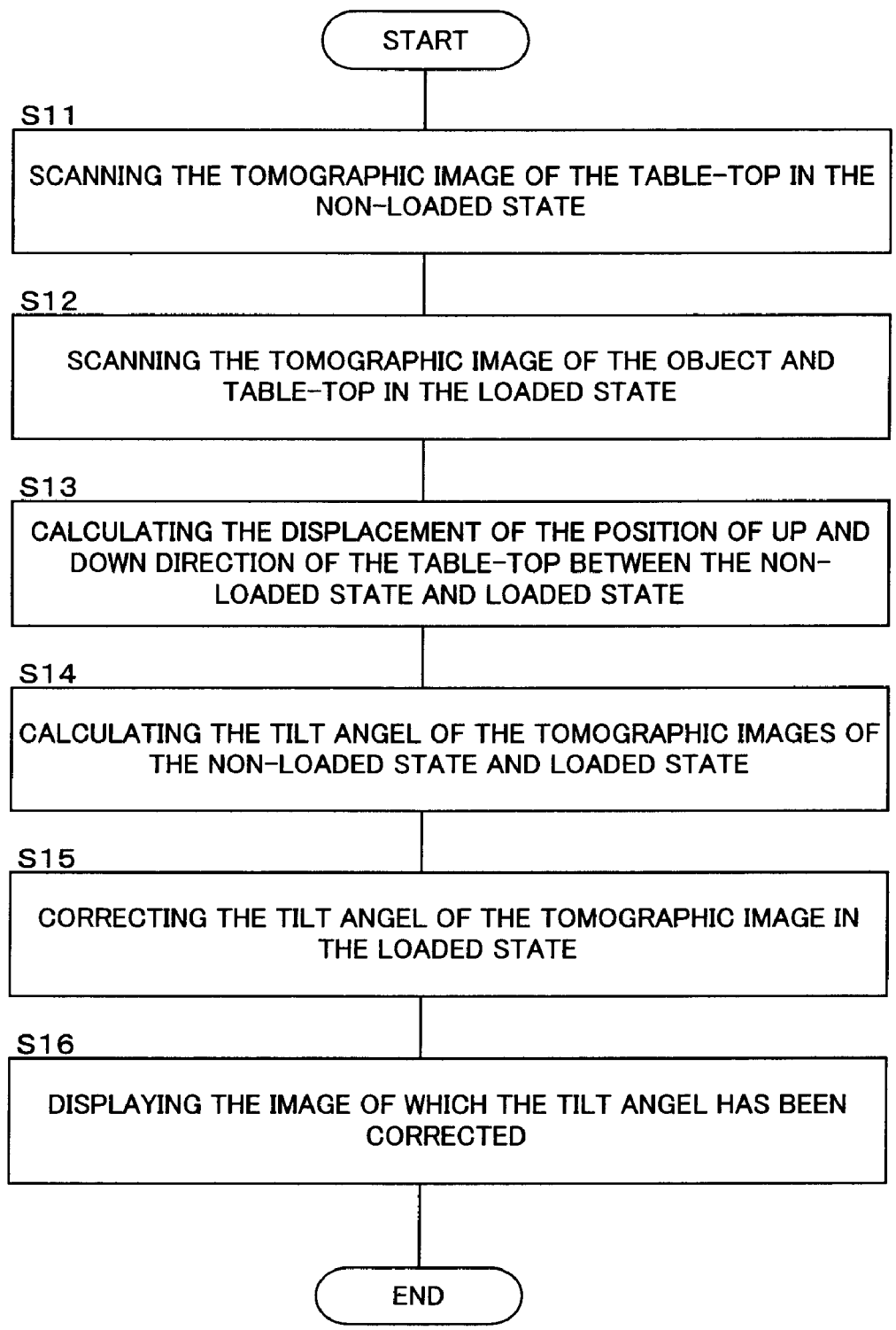
FIG. 10 is a flow chart showing n example of the preferred embodiment using the image diagnosis apparatus (X-ray CT apparatus) related to the invention.

Next, the second type of usage of the X-ray CT apparatus 1 is described hereinafter. The flowchart shown in FIG. 10 illustrates an example of the type of usage. This type of usage corrects the tilt of the tomographic image caused by the displacement of the patient table 31.

First, a summary of the type of usage shown in the flowchart in FIG. 10 is described, and then the operations of the X-ray CT apparatus 1 at each step of the used embodiment will be described.

Summary of the Second Type of Usage

An image of the patient table 31 in a state in which the object P is not placed on the patient table (tomographic image; axial image) is scanned (S11), and an image of the object P and patient table 31 in a state in which the object P is placed on the patient table (tomographic image; axial image) is also scanned (S12).

Next, the displacement calculation part 45 calculates the displacement between the location of the y-direction (y-coordinate value) in the non-loaded state and the y-direction (y-coordinate value) in the loaded state based on the image data of the acquired image in the non-loaded state and the image data of the acquired image in the loaded state (S13).

The above mentioned step S11 to S13 can be conducted in the same manner as in the step S1 to S3 in the above mentioned first type of usage.

Next, the tilt angle calculation part 46 calculates the tilt angle of the cross-section of the tomographic image in the non-loaded state that has been acquired in step S11 and the cross-section of the tomographic image in the loaded state that has been acquired in step S12 based on the displacement of the patient table 31 in the y-direction calculated in step S13 (S14).

After that, the correction image forming part 47 forms image data of the tomographic image of which tilt angle of the cross-section has been corrected according to the tilt angle calculated in step S14 (S15).

Lastly, the device control part 41 controls the monitor 5 to display an image based on the image data of which the tilt angle has been corrected (S16). Furthermore, this image data can be stored in a storage device such as a hard disk drive and saved in a media by a drive device that is not shown here.

Detail of the Operations at Each Step

A detailed description of steps S11 to S13 is omitted, because they can be conducted by the same method as the first type of usage.

(Step S14: Calculation of the Tilt Angle)

The processing of calculating the tilt angle between the cross-section of the tomographic image that can be acquired in the non-loaded state and the cross-section of the tomographic image that can be acquired in the loaded state is described hereinafter.

Figure 3A:
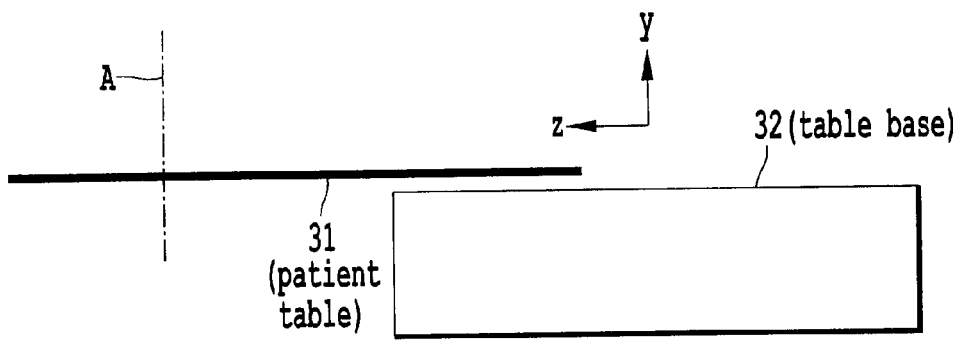
FIG. 3A is a schematic diagram explaining the patient table deflection occurred in the image diagnosis apparatus and showing the patient table in the non-loaded state.
Figure 3B:
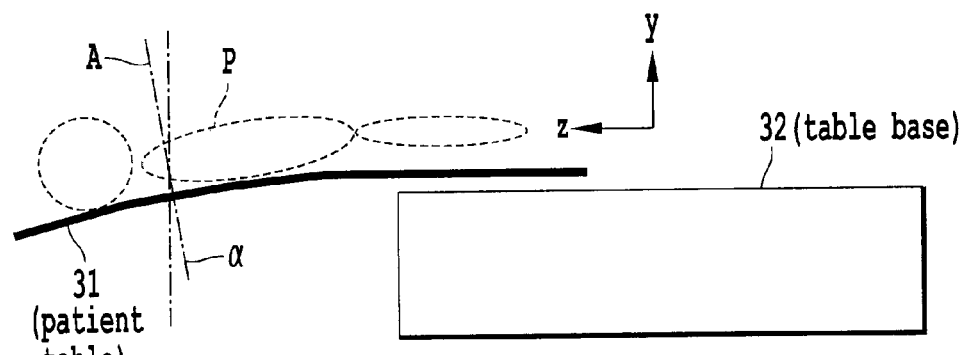
FIG. 3B is a schematic diagram explaining patient table deflection occurred in the image diagnosis apparatus and showing the patient table in the loaded state.
Figure 4:
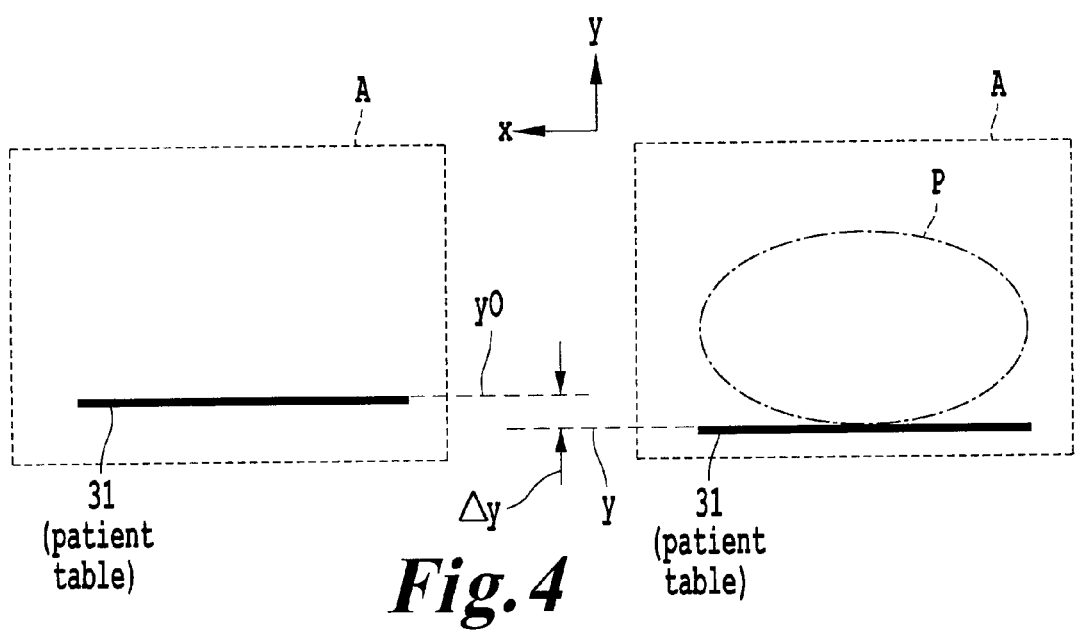
FIG. 4 is a schematic diagram explaining the patient table deflection occurred in the image diagnosis apparatus.

As shown in FIG. 3A, cross-section of the tomographic image that can be acquired in the non-loaded state is at right angle to the patient table 31 in the nearly horizontal state (a state parallel to xz-flat surface) (refer to the cross-section at slice location A). On the other hand, for the cross-section of the tomographic image that can be acquired in the loaded state, as shown in FIG. 3B, as the original slice location A tilts along with the tilt of the patient table 31 and object P, leading the slice location α stretched in the y-direction to become the actual slice location. In this step S14, the angle between the slice location A and slice location α is calculated based on the displacement of the patient table 31 in the y-direction. The example of the tilt angle computing processing executed by the tilt angle calculation part 46 is specifically described hereinafter.

For the first example, the displacement Δy(i) and Δy(i+1) have been calculated for each of the two reference positions (z-coordinate value=z(i), z(i+1)) indicated by the adjacent two markers 31(*i*) and 31(*i*+1)(i=1–n–1). Based on the displacement Δy(i) and Δy(i+1), the tilt angle calculation part 46 calculates the equation of the straight line connecting the two locations indicated as coordinate value(y(i), z(i)), (y(i+1), z(i+1)) on yz-flat surface.

Furthermore, it calculates the straight line inside the yz-flat surface that is right angle to the straight line (referred to as inclined straight line). Then, it calculates the tilt angle θ(i) of the inclined straight line to the y-direction (y-axis). This tilt angle θ(i) is the target tilt angle, in other words, the tilt angle between the cross-section (cross-section consists of inclined straight line) at the slice location A and the cross-section (xy-flat surface) at the slice location α in FIG. 3B.

The tilt angle calculation part 46 applies the value of θ(i) as the tilt angle at z=ζ to the location of any z-coordinate value ζ between z(i) and z(i+1).

In this example, it is preferred to have considerably many reference positions (markers 31(*i*)) and considerably narrow space between the adjacent reference positions z(i) and z(i+1) to improve the accuracy of the tilt angle.

For the second example of the processing of calculating the tilt angle, the tilt angle calculation part 46 first calculates the optimal curve line C passing through the n-unit of locations (y(i), z(i)) among the curve lines defined on the yz-flat surface based on the displacement Δy(i) determined for each reference position z(i). This computing processing can be performed by using any curve fitting algorithm.

And, to determine the tilt angle at any z=ζ, tilt angle calculation part 46 calculates the equation of the tangential line of the curve line C at z=ζ, and also calculates the equation of the straight line inside the yz-flat surface that is right angle to the tangential line (inclined straight line). After that, it calculates the tilt angle θ(ζ) of the inclined straight line to the y-direction (y-axis). This tilt angle θ(ζ) is the tilt angle between the cross-section (cross-section consists of inclined straight line) at the slice location A and the cross-section (xy-flat surface) at the slice location α in FIG. 3B.

In this example, it is also preferable to have many reference positions (markers 31(*i*)) to improve the accuracy of the tilt angle.

For the third example, the tilt angle is calculated when a helical scan is applied for the X-ray scan in step S11 and S12. In this case, the displacement status of the patient table 31 can be grasped as a nearly-curved line as described in the modified embodiment of the first type of usage. Then, the target tilt angle can be determined by the same manner as the above mentioned first example.

In addition, the target tilt angle can be determined by the same method as the above mentioned second specific example, giving a curve fitting to the nearly-curved form (a form of fine broken line) to express the displacement status as a curve.

(Step S15: Correction of the Tilt of the Tomographic Image)

The processing of calculating the tilt angle of the cross-section of the tomographic image that has been acquired in the loaded state is described hereinafter.

First, the correction image forming part 47 generates volume data and voxel data by performing known interpolation processing etc. to the image data of the tomographic image that has been acquired in step S12. This volume data comprises multiple voxels arranged in the x-direction, y-direction, and z-direction.

In addition, by performing MPR processing (Multi-Planar Reconstruction) to the volume data to generate (image data of) the tomographic image of which the cross-section being xy-flat surface, the tomographic image that has been acquired in step S12, in other words, tomographic image of the cross-section at the slice location a (parallel to the xy-flat surface) shown in FIG. 3B can be acquired.

The correction image forming part 47 performs MPR processing to the volume data to generate the image data of the tomographic image in a direction tilted at the tilt angle θ in +z-direction (refer to FIG. 3B) as calculated in step S14, in other words, in the direction in which the xy-flat surface is tilted at θ degrees in the +z-direction. Here, the rotation center when tilting the xy-flat surface may, for example, be on the body axis of the object (on the central axis of the rotation by the support drive section 25).

It allows to acquire the image data of the tomographic image of the cross-section at slice location A in FIG. 3B. This cross-section is parallel to the cross-section at slice location A in the non-loaded state shown in FIG. 3A.

The device control part 41 controls the monitor 5 to display the tomographic image based on the image data generated from the volume data by the correction image forming part 47 (step S16).

(Effects and Advantages of the Second Type of Usage)

According to the second type of usage of such X-ray CT apparatus 1, the patient table 31 in the non-loaded state is scanned separately to compare the location of the image of the patient table 31 in the non-loaded state with the location of the image of the patient table 31 in the loaded state, acquiring the tomographic image of which the tilt of the cross-section caused by the deflection from the patient table 31 by the weight of the object P is corrected.

Therefore, according to the first type of usage, effect of the deflection from the patient table 31 can be corrected without performing a major alteration to the hardware configuration of the apparatus such as adding a new device of system to an X-ray CT apparatus (medical image diagnosis apparatus) with a typical construction.

In addition, according to the second type of usage, since the tilt of the image is corrected by using the actual acquired image, the angle of tilting the patient table 31 (the tilt angle of the cross-section of the tomographic image) can be detected with high accuracy. Particularly, the tilt angle of the cross-section of the tomographic image can be detected with high accuracy by applying a helical scan or a curve fitting. Therefore, it can be preferably used for treatment planning for radiation therapy.

Furthermore, similar to the first type of usage, because there is no need to tilt the patient table 31 of gantry 2, the effect of deflection from the patient table 31 can be corrected simply and accurately, and the object P would not have to feel unnecessary discomfort.

Modified Embodiment of the Second Type of Usage

Similar modifications as the first type of usage can also be given to the second type of usage of the X-ray CT apparatus 1 appropriately. Alternatively, the following modified embodiment can be applied.

Other Modified Embodiment

As opposed to the above mentioned embodiment that have the markers 31(*i*) on only one side of the patient table 31, by having the markers on the both right and left sides to determine the displacement in vertical direction for each reference position at both right and left, misalignment of the quantity of deflection from the patient table 31 in longitudinal direction (x-direction) cab be detected. It allows to correct displacement of the tomographic image of the object P caused by the misalignment of the quantity of deflection from the patient table 31 in longitudinal direction, and allows to correct the tilt of the cross-section.

In addition, although the above mentioned embodiment described a construction that can execute both a processing of correcting displacement of an image in vertical direction (first type of usage) and a processing of correcting the tilt of the tomographic image (second type of usage), it is possible to employ a construction that can only execute one of the correction processes.

Here, to have only the first type of usage executable, the tilt angle calculation part 46 in FIG. 5 is not needed. In addition, regarding the processing content of the correction image forming part 47, it is enough to execute only the processing content described in the first type of usage or the second type of usage.

Moreover, while it may have both the processing content of the first type of usage and the processing content of the second type of usage executable, it may allow user to choose and specify one or both of these for execution. The method of specifying can be comprised of, for example, controlling the monitor 5 to display the prescribed operating screen and receiving input on the operation screen via an input device 6 such as a mouse.

Furthermore, although the patient table is moved toward the gantry in the above mentioned embodiment, it is possible to allow the gantry to move toward the patient table. Also, it is possible to have both the patient table and gantry movable. In either case, it is adequate when both the patient table and gantry are mutually movable.

Examples of the Usage

Examples of the usage of this invention for IMRT are described hereinafter. IMRT is a radiation therapy in which radiation is intensively delivered to a tumor tissue by combining multiple beams to have a different intensity in radiation.

First, an image is acquired using the medical image diagnosis apparatus related to this invention and the effect of the patient table deflection is corrected. A doctor or radiological technician refers to the acquired image to identify the location and shape of the tumor in the object, then decide the irradiated area of radiation and irradiated intensity. Thus the location and shape of the tumor can be grasped with high accuracy by using the image of which the effect of the patient table deflection has been corrected.

Next, a positioning operation is conducted. That is, placing markings on the body surface of the object to acquire an image, and confirming the irradiated area of radiation in reference with the acquired image, and then correcting the irradiated area, etc., as needed. Here, the irradiated area of radiation can also be decided with high accuracy by correcting the effect of the patient table deflection.

Next, an IMRT is applied on the object. For this purpose, the object is placed on the table of the treatment device.

The treatment device comprises a radiation source, Multi-leaf collimator and a computer. The Multi-leaf collimator alters the irradiated area and irradiated intensity of radiation toward the object by shielding partially the radiation generated from the radiation source. In addition, the treatment device can alter the direction of radiation.

The results of the above mentioned positioning operation are input to the computer. The computer controls the radiation source and Multi-leaf collimator based on the inputted contents to deliver radiation to the object. The treatment device thus puts the preferred irradiation embodiment into practice in accordance with the location and shape of the tumor.

Generally, the state in which the object is placed on the treatment device is different from the state in which the object is placed on the medical image diagnosis apparatus. Particularly for the medical image diagnosis apparatus, displacement occurs, such as downward misalignment of the part at the edge of the object (the edge near the gantry) or tilt of the slice location by the effect of the patient table deflection. As a result, the location of the tumor, etc., identified by the image, will not match the actual location of the tumor, etc., in the object that is placed on the treatment device and the location to which radiation is delivered will be misplaced.

By correcting the displacement of the acquired image according to the above embodiments, the location of the tumor, etc. in the object that is placed on the treatment device, in other words, the irradiated area, etc. of radiation can be specified with a high degree of accuracy, so it is possible to perform an IMRT effectively. Particularly, the irradiated area, etc., can be advantageously specified with a high degree of accuracy even when placing invisible marks.

In addition, this invention is also effective for radiation therapy other than IMRT.

What is claimed is:

1. A medical image diagnosis apparatus, comprising:
    a patient table;
    a data acquisition part configured to scan the patient table in a non-loaded state in which an object is not placed on the patient table to acquire first scan data and to scan the patient table and an object in a loaded state in which the object is placed on the patient table to acquire second scan data;
    an image data-forming part configured to form a first image based on the first scan data and a second image based on the second scan data;
    a displacement calculation part configured to calculate displacement of the patient table in the non-loaded state and in the loaded state based on the first image and the second image; and
    a correction part configured to correct the position of the second image based on the displacement,
    wherein the image data-forming part is configured to
        form the first image including a tomographic image of the patient table; and
        form the second image including the tomographic image of the patient table and the tomographic image of the object,
    wherein the displacement calculation part is configured to
        determine the position of the tomographic image of the patient table in the first image based on the first image;
        determine the position of the tomographic image of the patient table in the second image based on the second image; and
        calculate the difference of the determined positions of the tomographic images of the patient table for the first image and the second image, respectively, as the displacement,
    the apparatus further comprising a patient table drive configured to move the patient table in a specified patient table moving direction, wherein a plurality of reference positions in the specified patient table moving direction are preset for the patient table, and for each of the plurality of reference positions, the image data-forming part is configured to
        form the first image including a tomographic image of the patient table at said reference position; and
        form the second image including the tomographic image of the patient table and the tomographic image of the object at said reference position, and the displacement calculation part is configured to
        for each of the plurality of reference positions, calculate the difference between positions of the tomographic image of the patient table of the first image and the second image as the displacement at said reference position; and
        calculate displacement at an intermediate position of two adjacent reference positions of the plurality of reference positions based on each of said displacements of the two reference positions; and
    the correction part corrects the position of second image at the intermediate position based on displacement at the intermediate position.

2. A medical image diagnosis apparatus, comprising:
    a patient table;
    a data acquisition part configured to scan the patient table in a non-loaded state in which an object is not placed on the patient table to acquire first scan data and to scan the patient table and an object in a loaded state in which the object is placed on the patient table to acquire second scan data;
    an image data-forming part configured to form a first image based on the first scan data and a second image based on the second scan data;
    a displacement calculation part configured to calculate displacement of the patient table in the non-loaded state and in the loaded state based on the first image and the second image; and
    a correction part configured to correct the position of the second image based on the displacement,
    wherein the displacement calculation part calculates displacement in a vertical direction of the patient table;
    the correction part corrects the position in the vertical direction of the second image;
    the image data-forming part is configured to
        form the first image including a tomographic image of the patient table; and
        form the second image including the tomographic image of the patient table and the tomographic image of the object; and
    the displacement calculation part is configured to
        determine the position of the tomographic image of the patient table in the first image based on the first image;
        determine the position of the tomographic image of the patient table in the second image based on the second image; and
        calculate the difference of the determined positions of the tomographic images of the patient table for the first image and the second image, respectively, as the displacement,
    the apparatus further comprising a patient table drive configured to move the patient table in a specified patient table moving direction, wherein a plurality of reference positions in the specified patient table moving direction are preset for the patient table, and for each of the plurality of reference positions, the image data-forming part is configured to
        form the first image including a tomographic image of the patient table at said reference position; and form the second image including the tomographic image of the patient table and the tomographic image of the object at said reference position, and the displacement calculation part is configured to for each of the plurality of reference positions, calculate the difference between positions of the tomographic image of the patient table of the first image and the second image as the displacement at said reference position; and calculate displacement at an intermediate position of two adjacent reference positions of the plurality of reference positions based on each of said displacements of the two reference positions; and the correction part corrects the position of second image at the intermediate position based on displacement at the intermediate position.

3. A medical image diagnosis apparatus, comprising:

a patient table;

a data acquisition part configured to scan the patient table in a non-loaded state in which an object is not placed on the patient table to acquire first scan data and to scan the patient table and an object in a loaded state in which the object is placed on the patient table to acquire second scan data;

an image data-forming part configured to form a first image based on the first scan data and a second image based on the second scan data;

a displacement calculation part configured to calculate displacement of the patient table in the non-loaded state and in the loaded state based on the first image and the second image; and a correction part configured to correct the position of the second image based on the displacement, wherein the image data-forming part is configured to form the first image including a tomographic image of the patient table; and form the second image including the tomographic image of the patient table and the tomographic image of the object, wherein the displacement calculation part is configured to determine the position of the tomographic image of the patient table in the first image based on the first image;

determine the position of the tomographic image of the patient table in the second image based on the second image; and calculate the difference of the determined positions of the tomographic images of the patient table for the first image and the second image, respectively, as the displacement, the apparatus further comprising a patient table drive configured to move the patient table in a specified patient table moving direction, wherein a plurality of reference positions in the specified patient table moving direction are preset for the patient table, and for each of the plurality of reference positions, the image data-forming part is configured to form the first image including a tomographic image of the patient table at said reference position; and form the second image including the tomographic image of the patient table and the tomographic image of the object at said reference position, and the displacement calculation part is configured to calculate a curve line approximating the plurality of reference positions for each of the first image and the second image; and calculate displacement of the patient table at an intermediate position of two adjacent reference positions of the plurality of reference positions based on the curve line of the first image and the curve line of the second image; and the correction part corrects the position of the second image at the intermediate position based on the displacement at the intermediate position.

4. A medical image diagnosis apparatus, comprising:

a patient table;

a data acquisition part configured to scan the patient table in a non-loaded state in which an object is not placed on the patient table to acquire first scan data and to scan the patient table and an object in a loaded state in which the object is placed on the patient table to acquire second scan data;

an image data-forming part configured to form a first image based on the first scan data and a second image based on the second scan data;

a displacement calculation part configured to calculate displacement of the patient table in the non-loaded state and in the loaded state based on the first image and the second image; and a correction part configured to correct the position of the second image based on the displacement, wherein the displacement calculation part calculates displacement in a vertical direction of the patient table;

the correction part corrects the position in the vertical direction of the second image;

the image data-forming part is configured to form the first image including a tomographic image of the patient table; and form the second image including the tomographic image of the patient table and the tomographic image of the object; and the displacement calculation part is configured to determine the position of the tomographic image of the patient table in the first image based on the first image;

determine the position of the tomographic image of the patient table in the second image based on the second image; and calculate the difference of the determined positions of the tomographic images of the patient table for the first image and the second image, respectively, as the displacement, the apparatus further comprising a patient table drive configured to move the patient table in a specified patient table moving direction, wherein a plurality of reference positions in the specified patient table moving direction are preset for the patient table, and for each of the plurality of reference positions, the image data-forming part is configured to form the first image including a tomographic image of the patient table at said reference position; and form the second image including the tomographic image of the patient table and the tomographic image of the object at said reference position, and the displacement calculation part is configured to calculate a curve line approximating the plurality of reference positions for each of the first image and the second image; and calculate displacement of the patient table at an intermediate position of two adjacent reference positions of the plurality of reference positions based on the curve line of the first image and the curve line of the second image; and the correction part corrects the position of the second image at the intermediate position based on the displacement at the intermediate position.

5. A medical image diagnosis apparatus, comprising:
a patient table;
a patient table drive configured to move the patient table in a specified patient table moving direction;
a data acquisition part configured to scan the patient table in a non-loaded state in which an object is not placed on the patient table to acquire first scan data for each of a plurality of positions in the specified patient table moving direction and to scan the patient table and the object in a loaded state in which the object is placed on the patient table to acquire second scan data for each of the plurality of positions;
an image data-forming part configured to form a first tomographic image based on the first scan data and to form a second tomographic image based on the second scan data, for each of the plurality of positions;
a displacement calculation part configured to calculate displacement of the patient table in the non-loaded state and in the loaded state based on the first tomographic image and the second tomographic image for each of the plurality of positions; and
a tilt angle calculation part configured to calculate the tilt angle made by a cross-section of the first tomographic image and a cross-section of the second tomographic image at each of the plurality of positions based on the displacement, wherein
the image data-forming part forms a new tomographic image of the object for the cross-section of the first tomographic image based on the tilt angle for each of the plurality of positions.

6. A medical image diagnosis apparatus according to claim 5, wherein the data acquisition part comprises:
an X-ray generator;
an X-ray detector located at the position opposite to the X-ray generator over the patient table;
a rotary drive configured to rotate and to drive the X-ray generator and the X-ray detector about the specified patient table moving direction as the axis of rotation; and
a scan controller configured to simultaneously control the patient table drive and the rotary drive to execute a helical scanning to the patient table in the non-loaded state to acquire the first scan data for each of the plurality of positions, and to execute a helical scanning to the patient table and the object in the loaded state to acquire the second scan data for each of the plurality of positions.

7. A control method for medical image diagnosis apparatus including a patient table; a patient table drive configured to move the patient table to a specified patient table moving direction; a data acquisition part configured to scan an object placed on the patient table to acquire scan data; an image data-forming part configured to form an image based on the scan data; and an image data processing part configured to process the formed image, the control method comprising:
in a non-loaded state in which an object is not placed on the patient table, controlling the data acquisition part to scan the patient table to acquire first scan data for each of a plurality of positions of the specified patient table moving directions, and controlling the image data-forming part to form a first tomographic image based on the first scan data for each of the plurality of positions;
in a loaded state in which an object is placed on the patient table, controlling the data acquisition part to scan the patient table and the object to acquire second scan data for each of the plurality of positions, and controlling the image data-forming part to form a second tomographic image based on the second scan data for each of the plurality of positions;
calculating, by the image data processing part of the medical image diagnosis apparatus, displacement of the patient table in the non-loaded state and in the loaded state based on the first tomographic image and the second tomographic image for each of the plurality of positions, and calculating a tilt angle formed by a cross-section of the first tomographic image and a cross-section of the second tomographic image for each of the plurality of positions based on the displacement; and
controlling the image data-forming part to form a new tomographic image of the object in the cross-section of the first tomographic image based on the tilt angle for each of the plurality of positions.

* * * * *